US011419598B1

(12) United States Patent
Ferguson

(10) Patent No.: US 11,419,598 B1
(45) Date of Patent: Aug. 23, 2022

(54) SOFT SUTURE ANCHOR

(71) Applicant: RIVERPOINT MEDICAL, LLC, Portland, OR (US)

(72) Inventor: Patrick Edward Ferguson, Portland, OR (US)

(73) Assignee: RIVERPOINT MEDICAL, LLC, Portland, OR (US)

( * ) Notice: Subject to any disclaimer, the term of this patent is extended or adjusted under 35 U.S.C. 154(b) by 326 days.

(21) Appl. No.: 16/184,566

(22) Filed: Nov. 8, 2018

Related U.S. Application Data

(63) Continuation-in-part of application No. 16/055,464, filed on Aug. 6, 2018, now Pat. No. 11,076,844, which is a continuation of application No. 13/886,126, filed on May 2, 2013, now Pat. No. 10,070,856.

(60) Provisional application No. 61/642,733, filed on May 4, 2012, provisional application No. 61/642,433, filed on May 3, 2012.

(51) Int. Cl.
*A61B 17/04* (2006.01)

(52) U.S. Cl.
CPC .................. *A61B 17/0401* (2013.01)

(58) Field of Classification Search
CPC ............ A61F 2/0811; A61F 2002/0817; A61F 2002/0823; A61F 2002/0835; A61F 2002/0847; A61F 2002/0852; A61B 17/0401; A61B 2017/0475; A61B 2017/0474; A61B 2017/0496; A61B 2017/0409
See application file for complete search history.

(56) References Cited

U.S. PATENT DOCUMENTS

| 7,959,650 | B2 | 6/2011 | Kaiser et al. |
| 8,088,130 | B2 | 1/2012 | Kaiser et al. |
| 8,231,654 | B2 | 7/2012 | Kaiser et al. |
| 10,070,856 | B1 | 9/2018 | Black et al. |
| 2005/0149118 | A1 | 7/2005 | Koyfman |
| 2007/0185532 | A1 | 8/2007 | Stone et al. |
| 2011/0098727 | A1* | 4/2011 | Kaiser ............... A61B 17/0401 606/144 |
| 2011/0208239 | A1* | 8/2011 | Stone ................. A61B 17/0485 606/228 |
| 2011/0270278 | A1 | 11/2011 | Overes et al. |
| 2012/0197271 | A1 | 8/2012 | Astorino et al. |

(Continued)

*Primary Examiner* — Richard G Louis
*Assistant Examiner* — Chima U Igboko
(74) *Attorney, Agent, or Firm* — Timothy E. Siegel Patent Law, PLLC; Timothy E. Siegel

(57) ABSTRACT

A soft anchor construct, having a cross-member suture of braided suture material and a cinching suture that has a first end and a second end. The cinching suture, starting at its first end, extends to the cross-member suture, and engages and traverses the cross-member suture at a first central point and then extends from the first central point to a first lateral point, and engages and traverses the cross-member suture at the first lateral point. The cinching suture then extends from the first lateral point to a second lateral point, opposed to the first lateral point, and engages and traverses the cross-member suture at the second lateral point and then extends from the second lateral point to a second central point and engages and traverses the cross-member suture at the second central point and extends from the second central point to the second end.

9 Claims, 29 Drawing Sheets

(56) References Cited

U.S. PATENT DOCUMENTS

2013/0110165 A1  5/2013  Burkhart et al.
2015/0142050 A1* 5/2015  Ferguson ........... A61B 17/0485
                                                606/228
2018/0338756 A1 11/2018  Black et al.

* cited by examiner

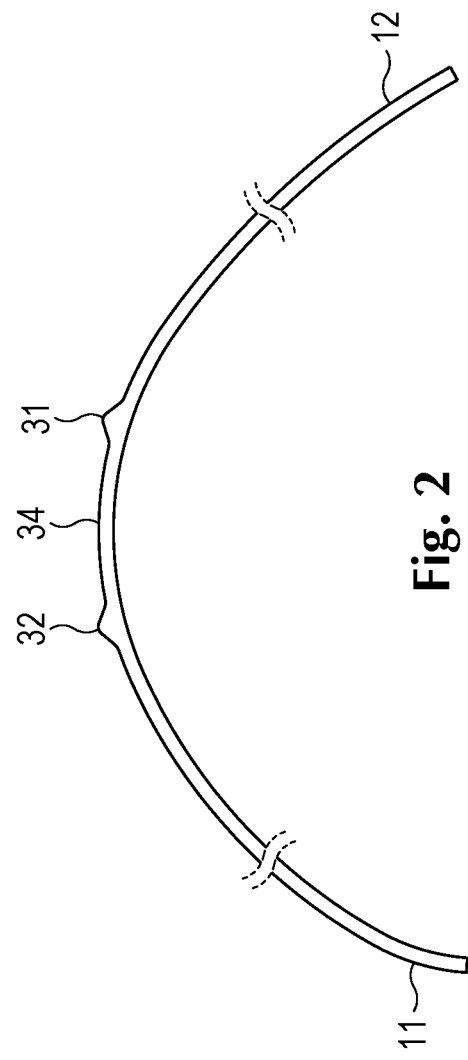
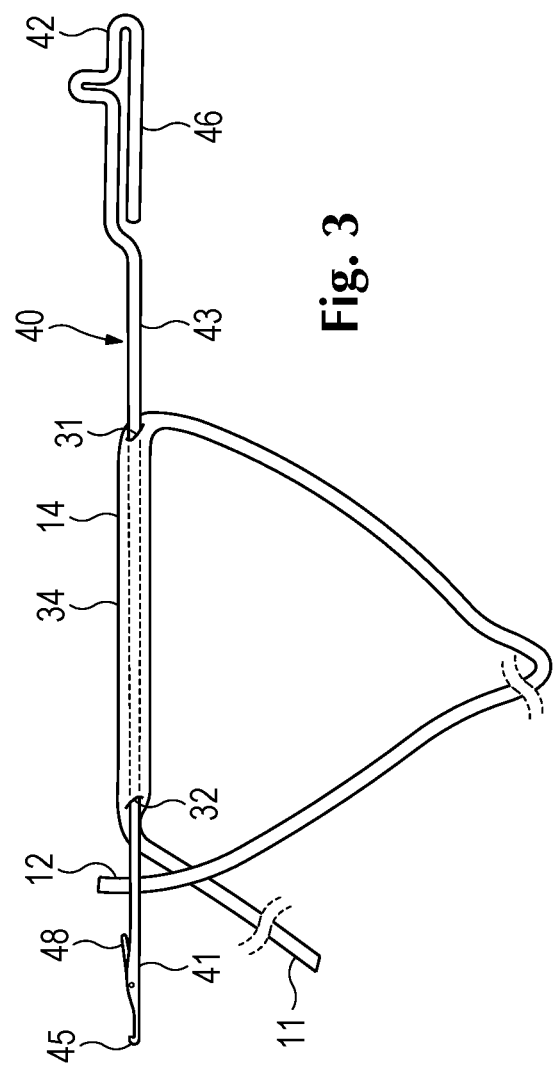
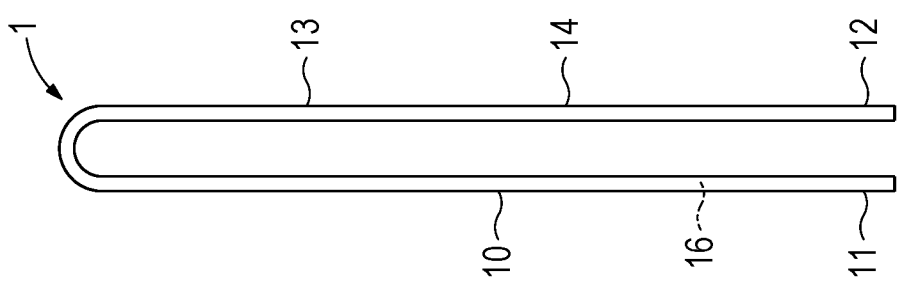

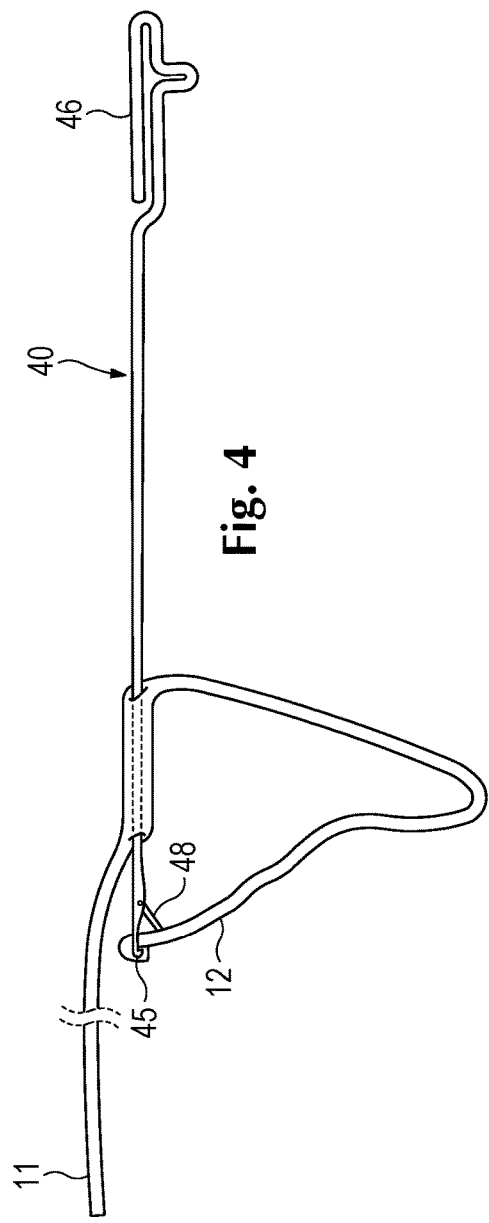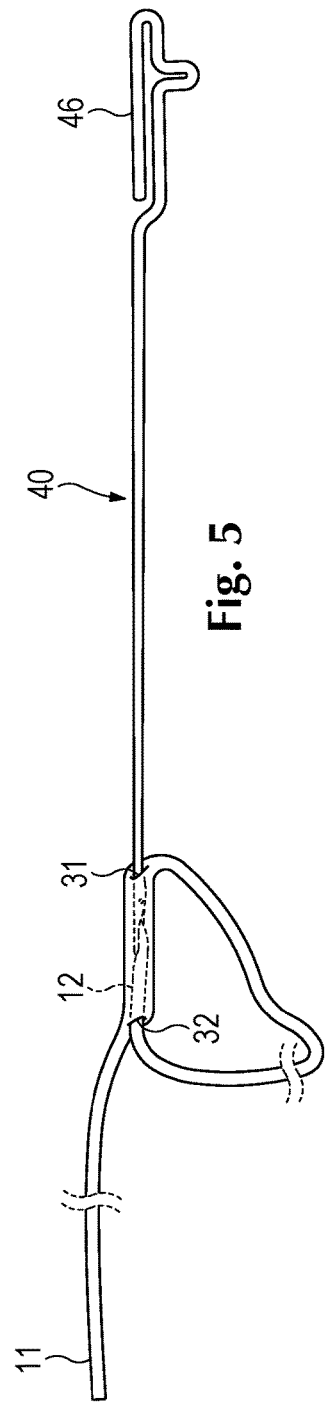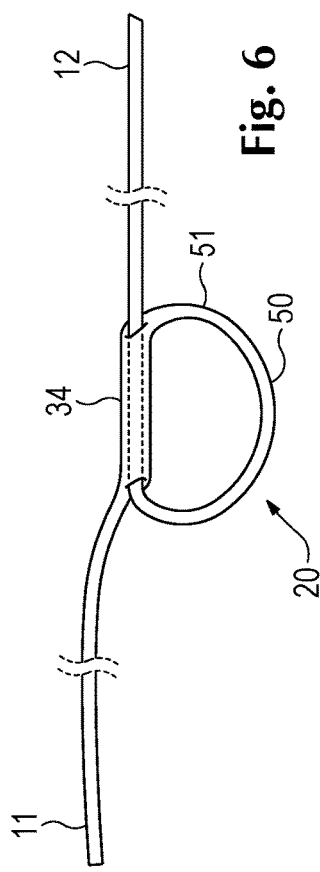

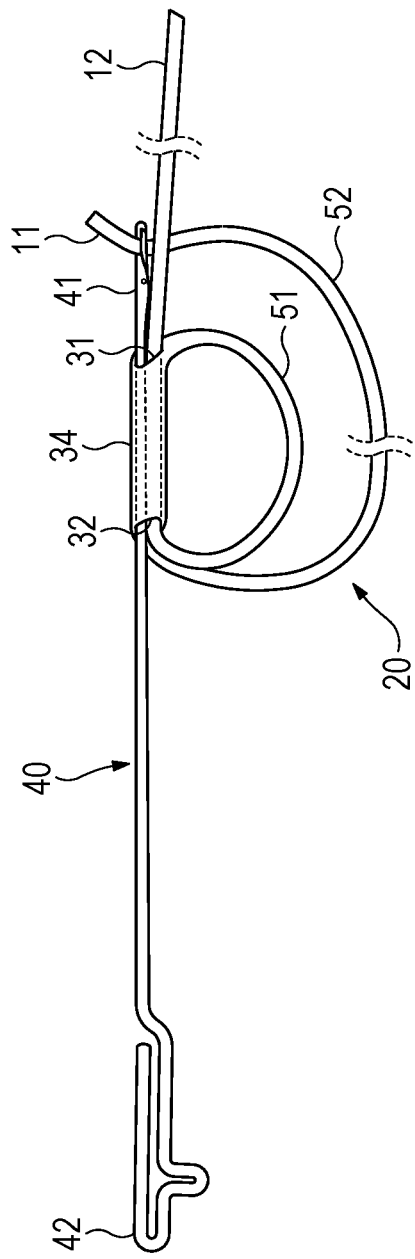
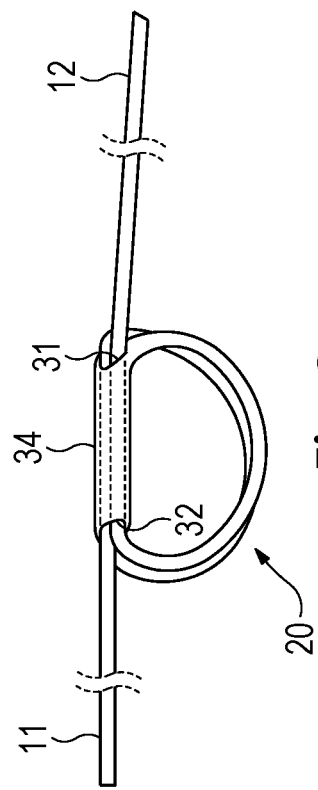
Fig. 7
Fig. 8

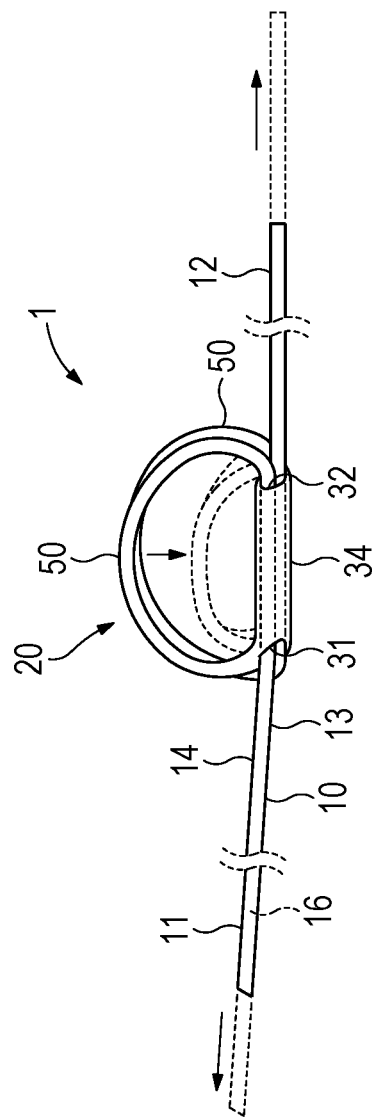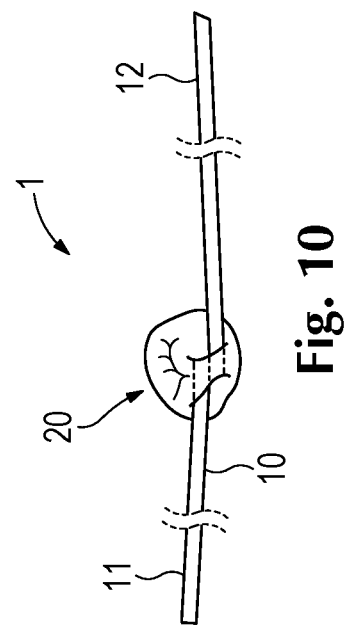

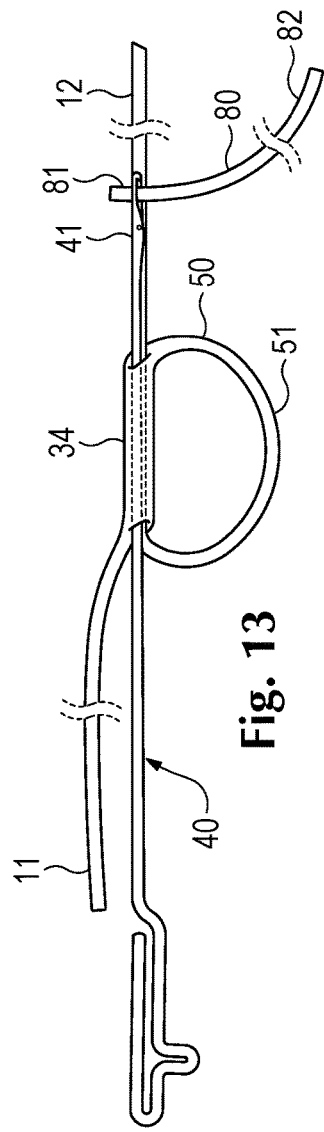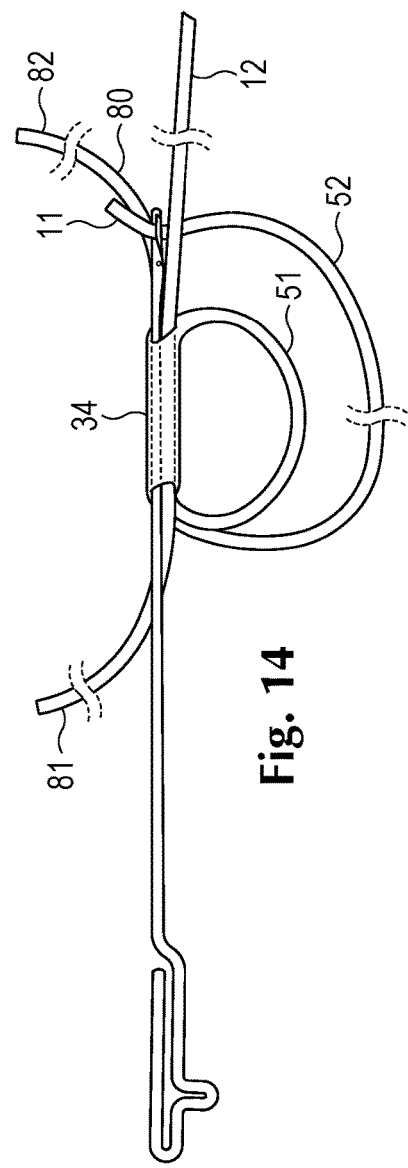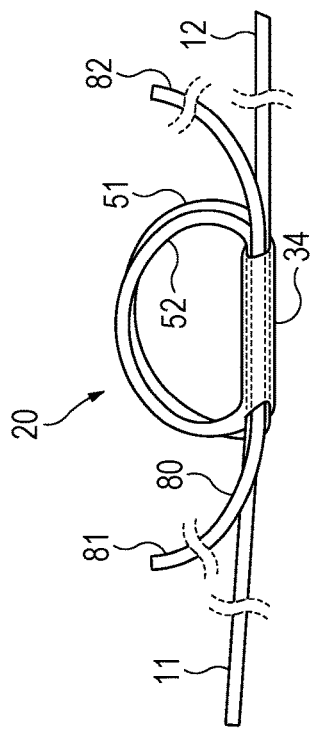

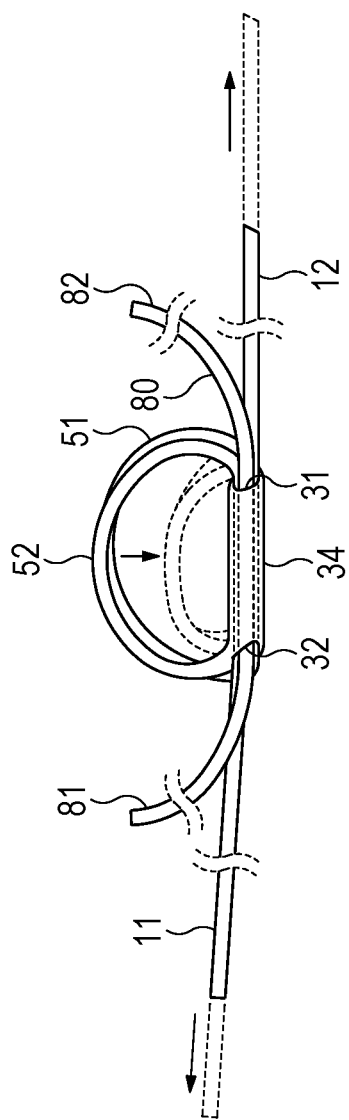
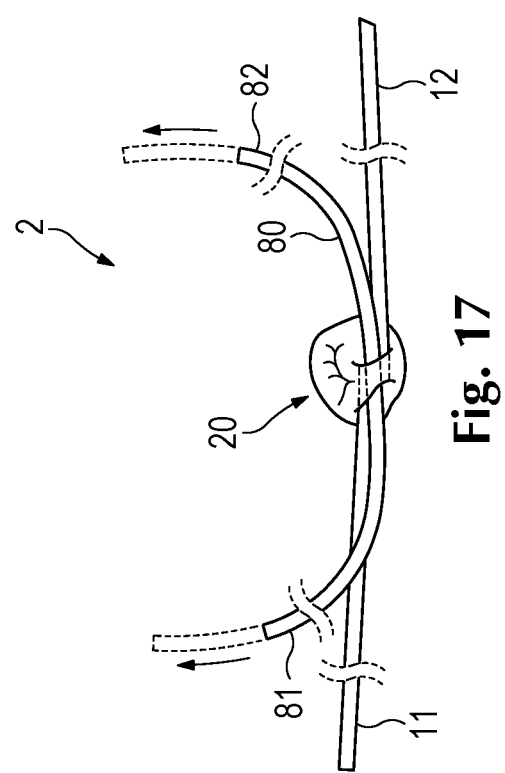

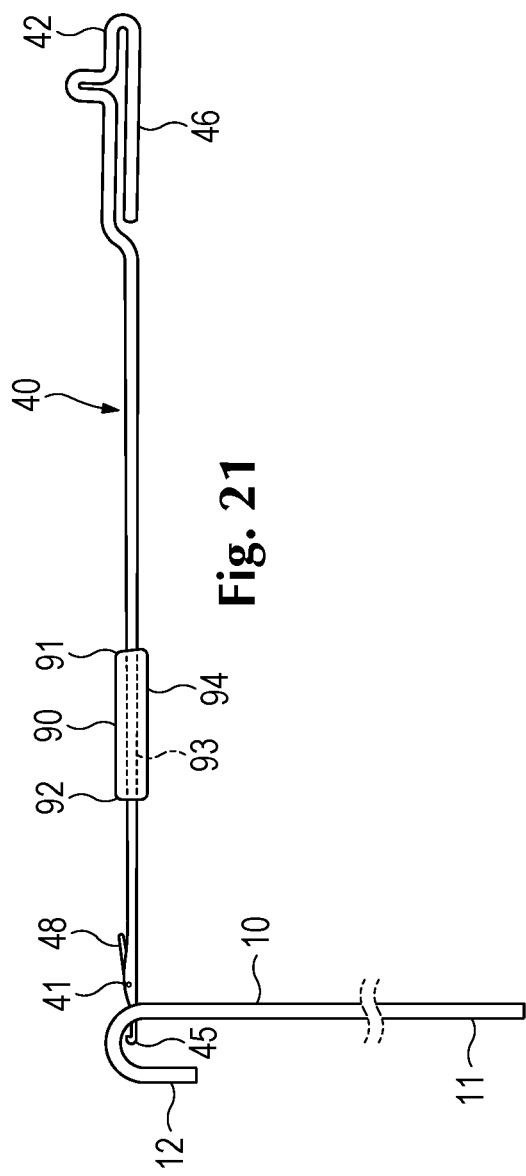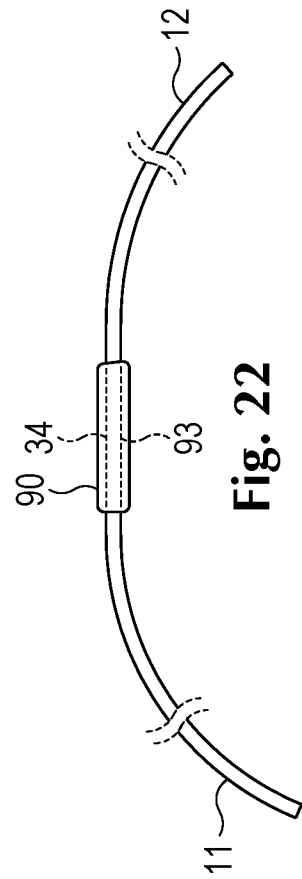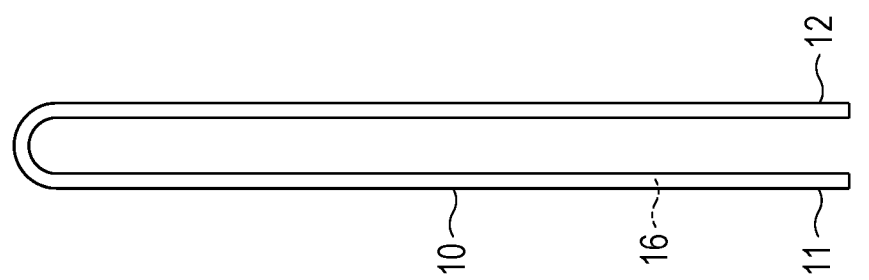

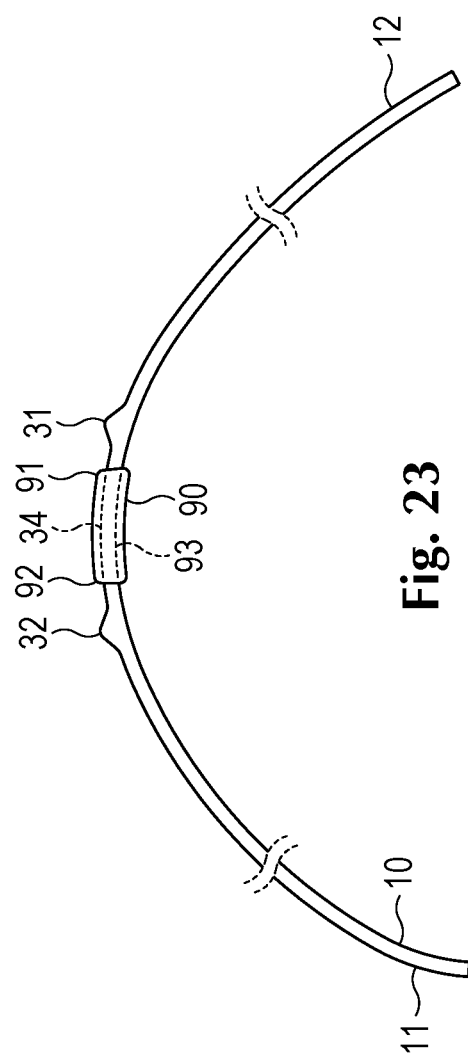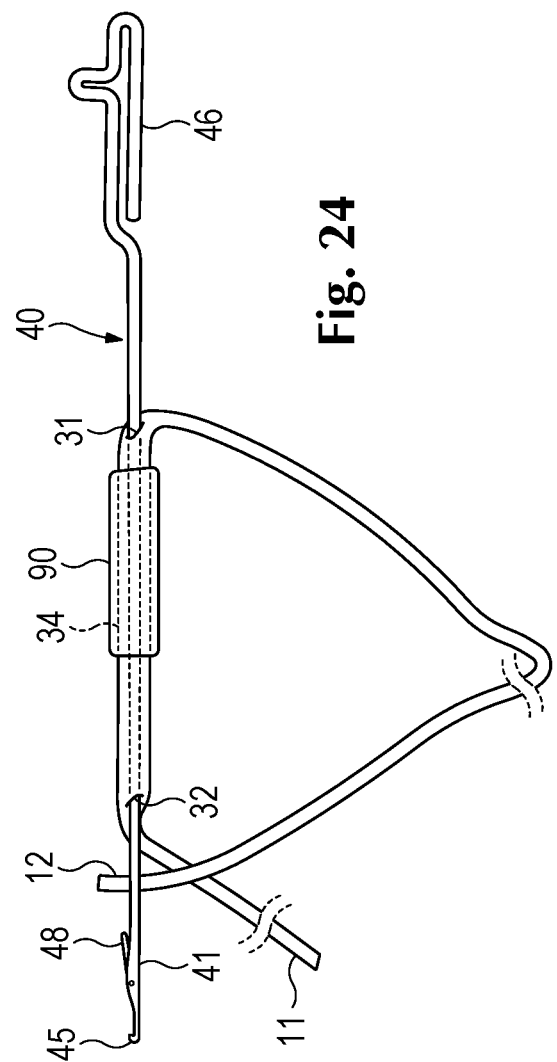

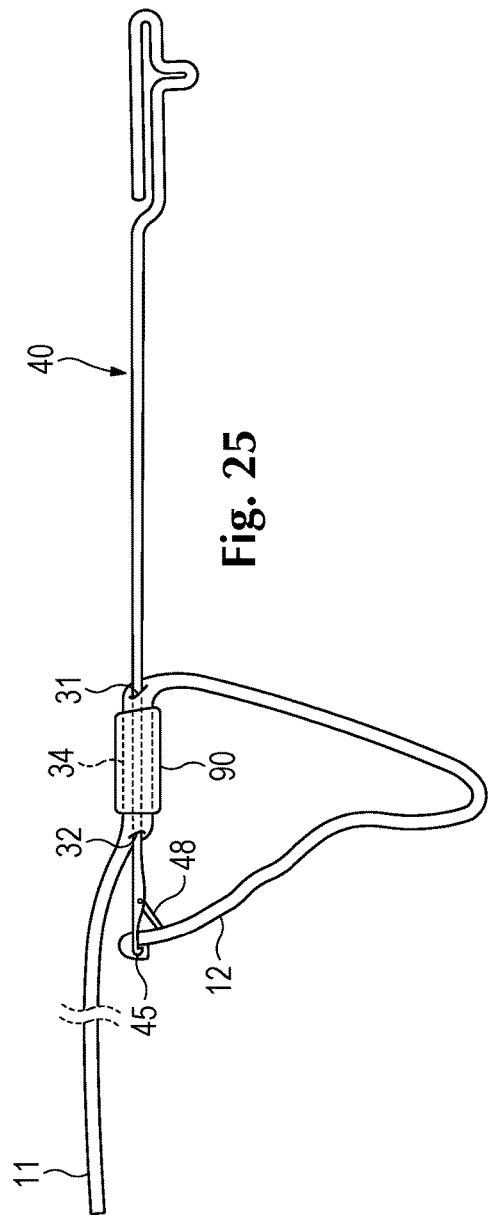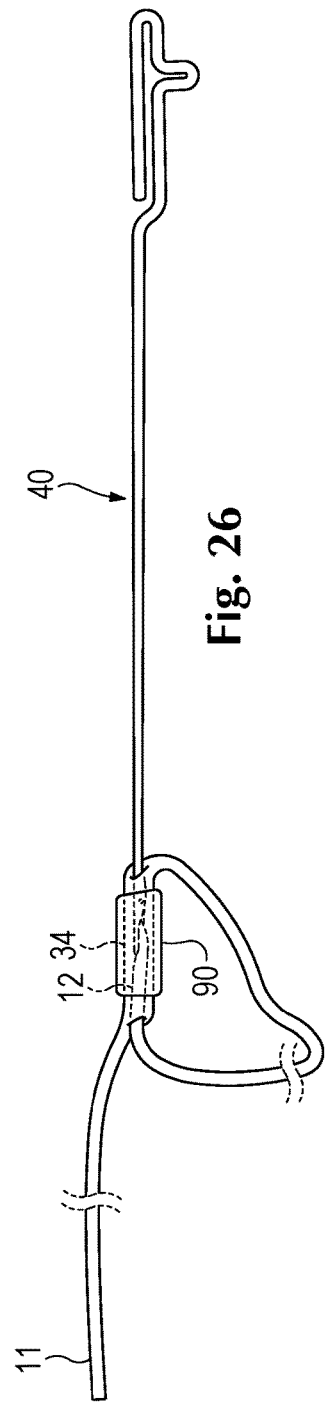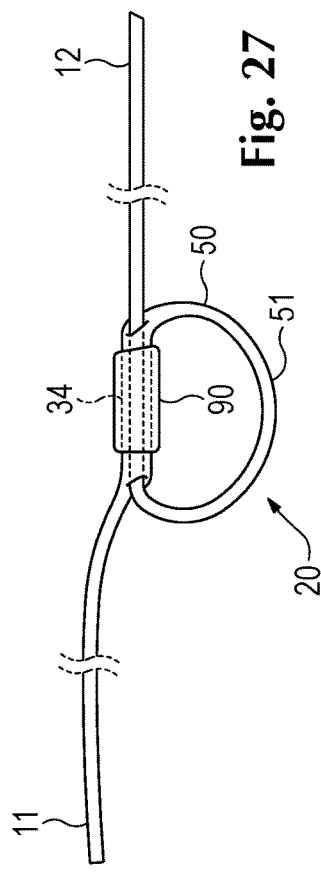

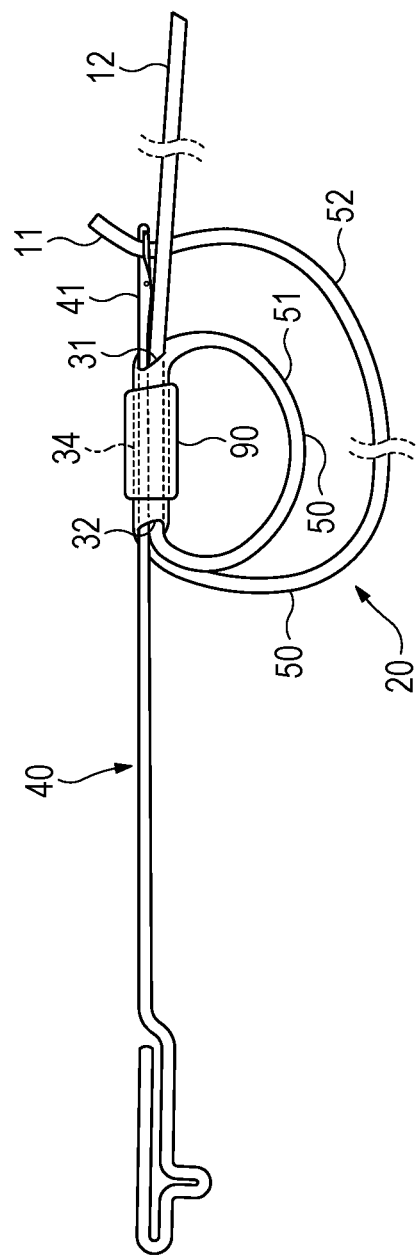
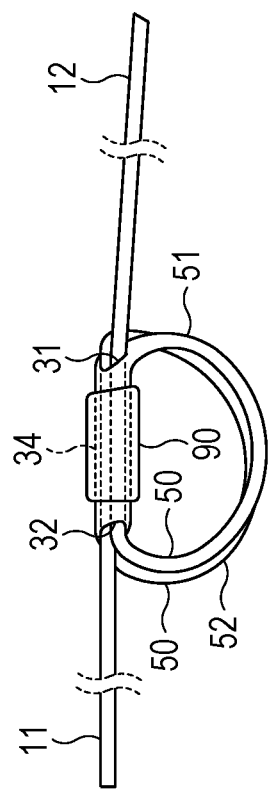

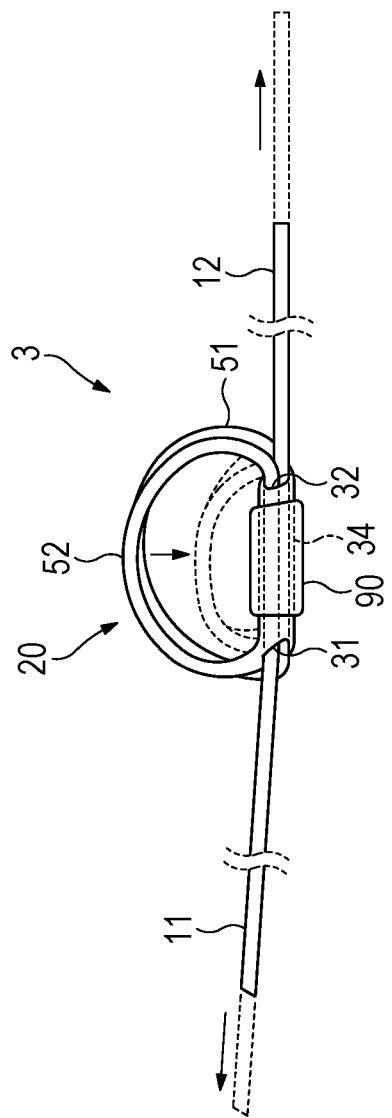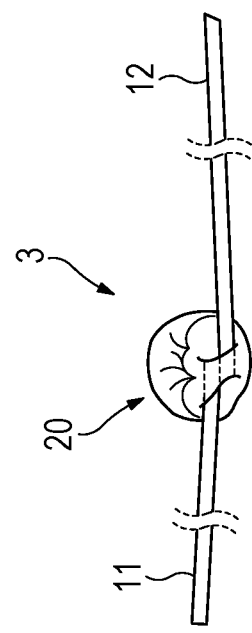

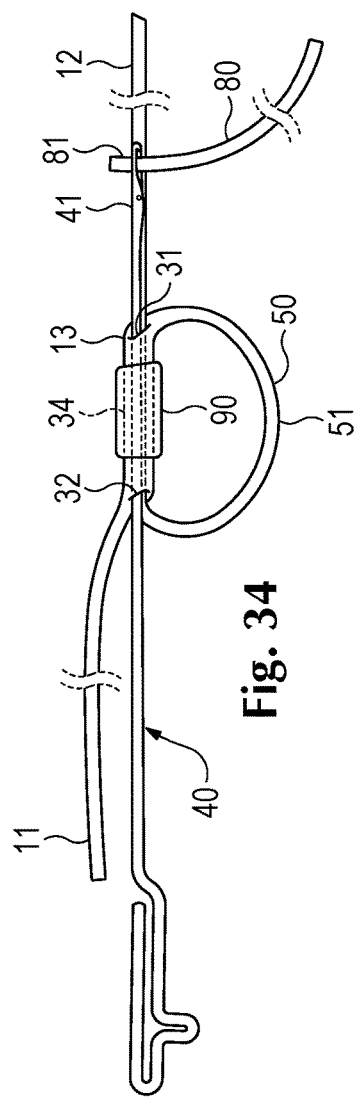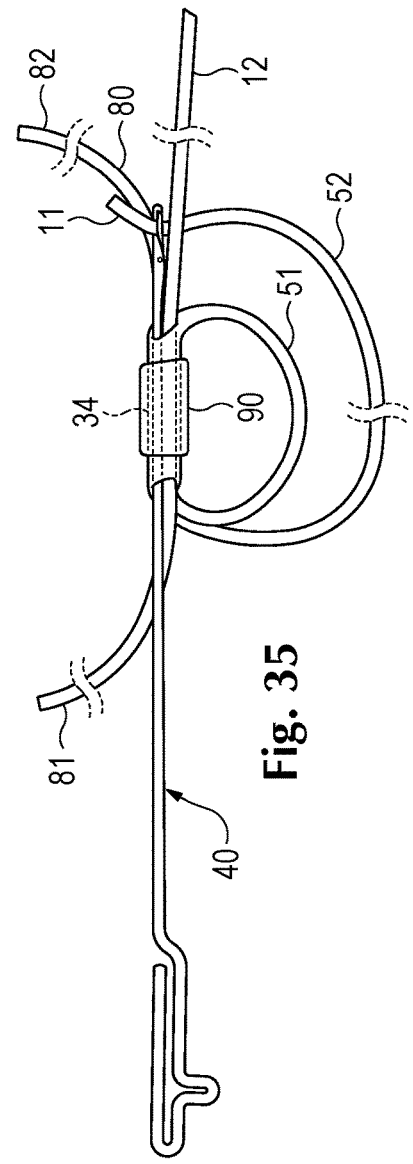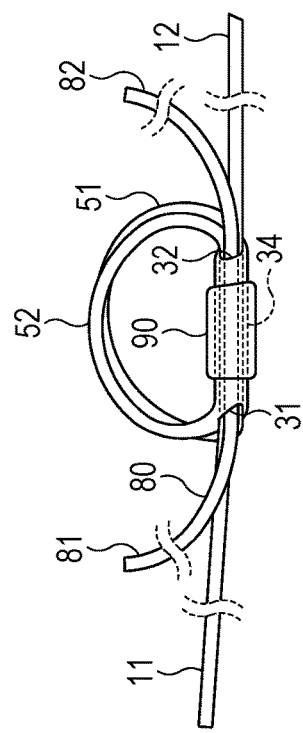

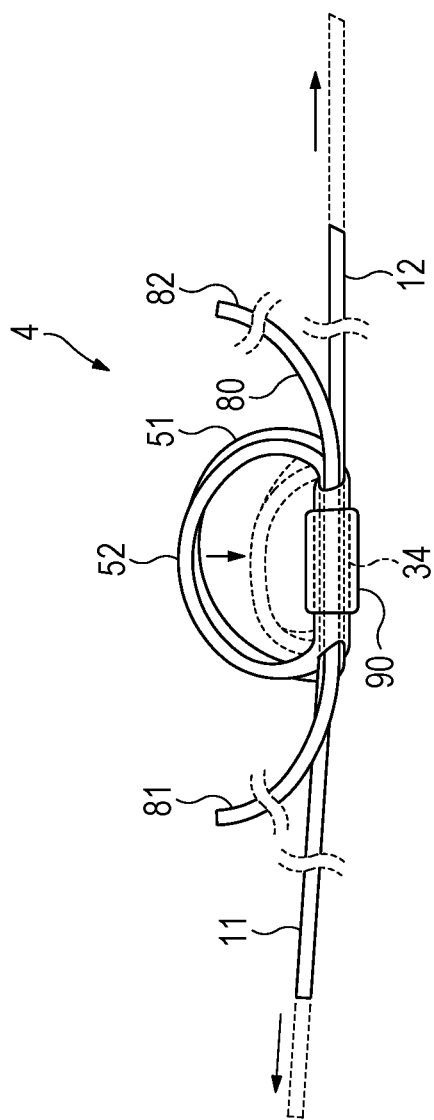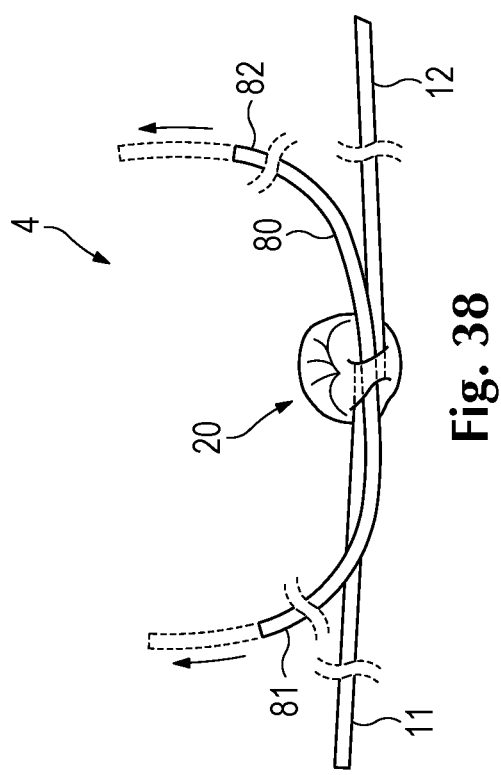

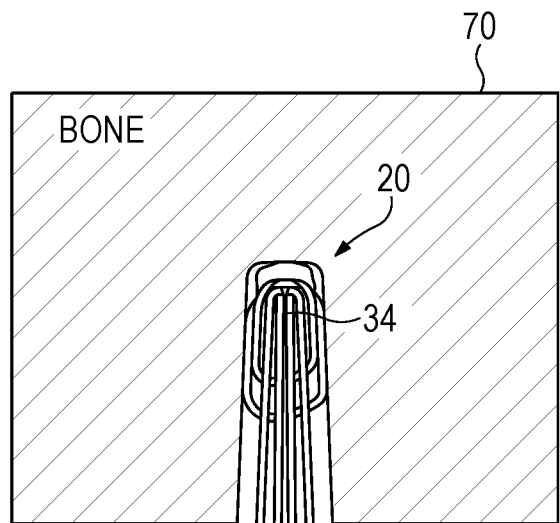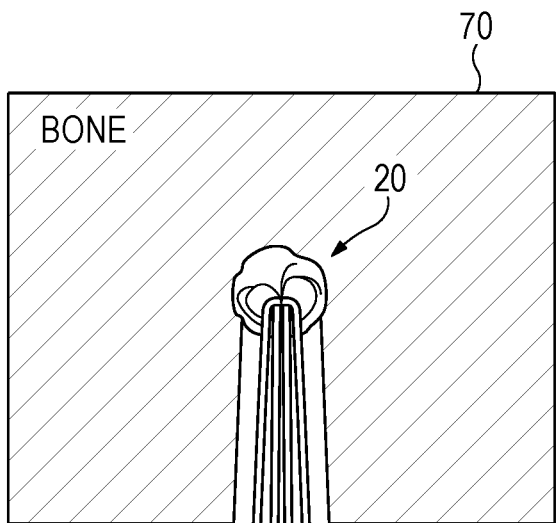
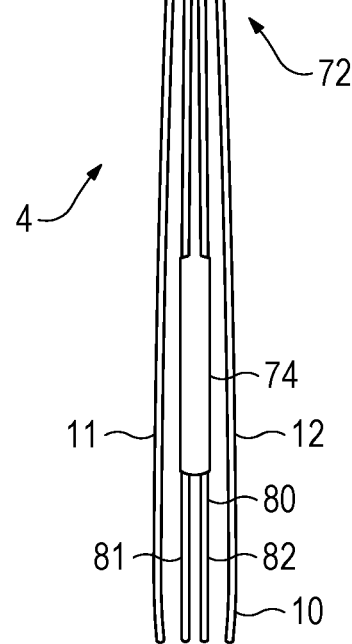
Fig. 39
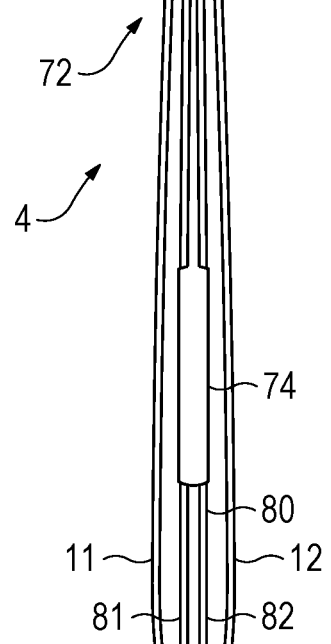
Fig. 40

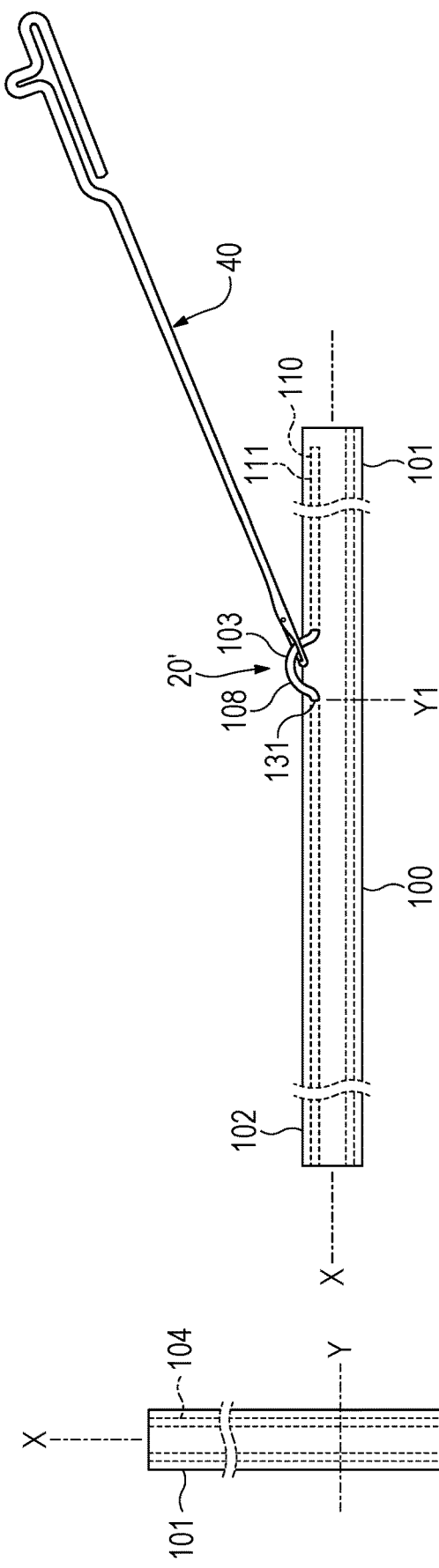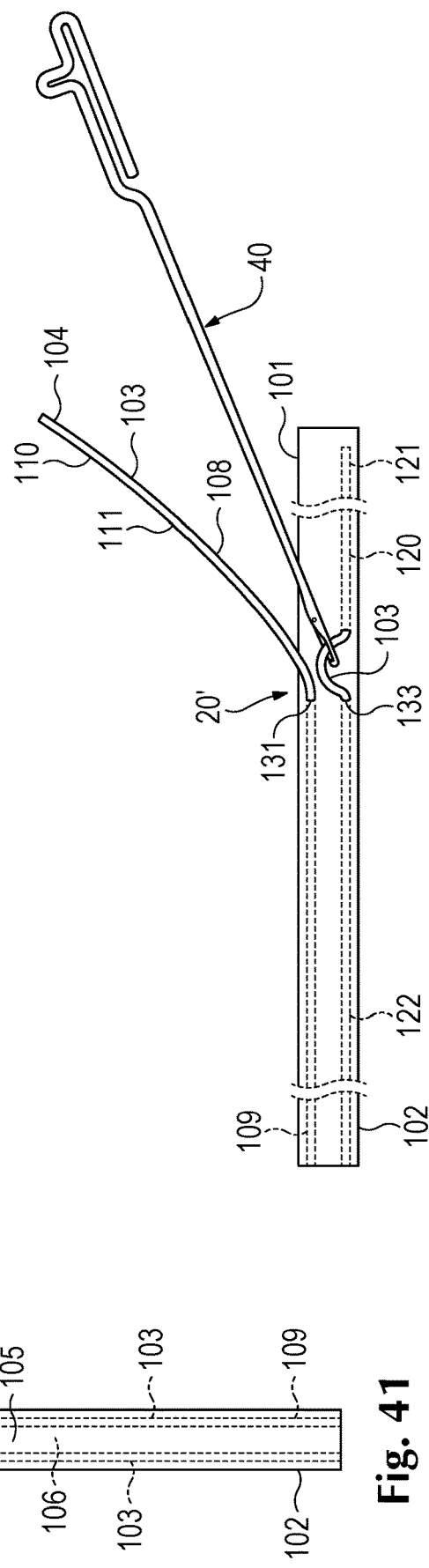

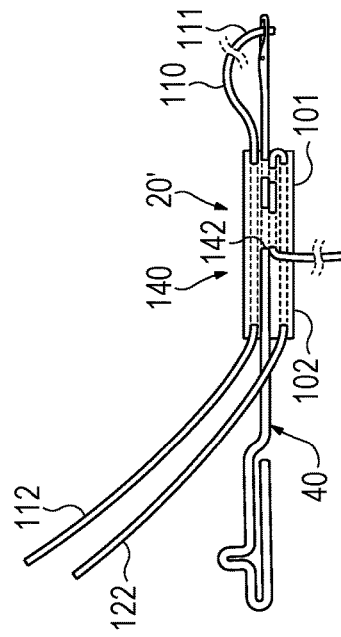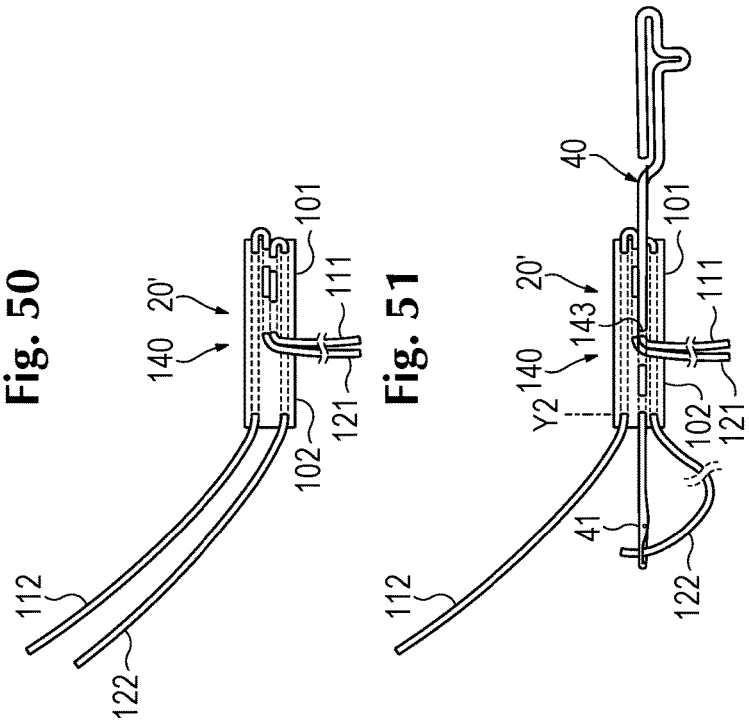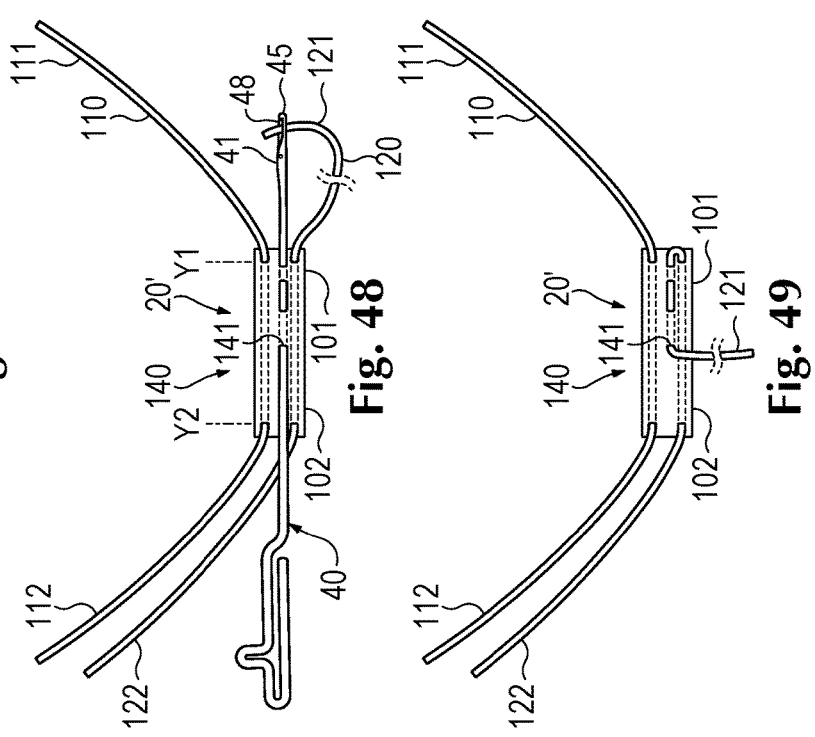

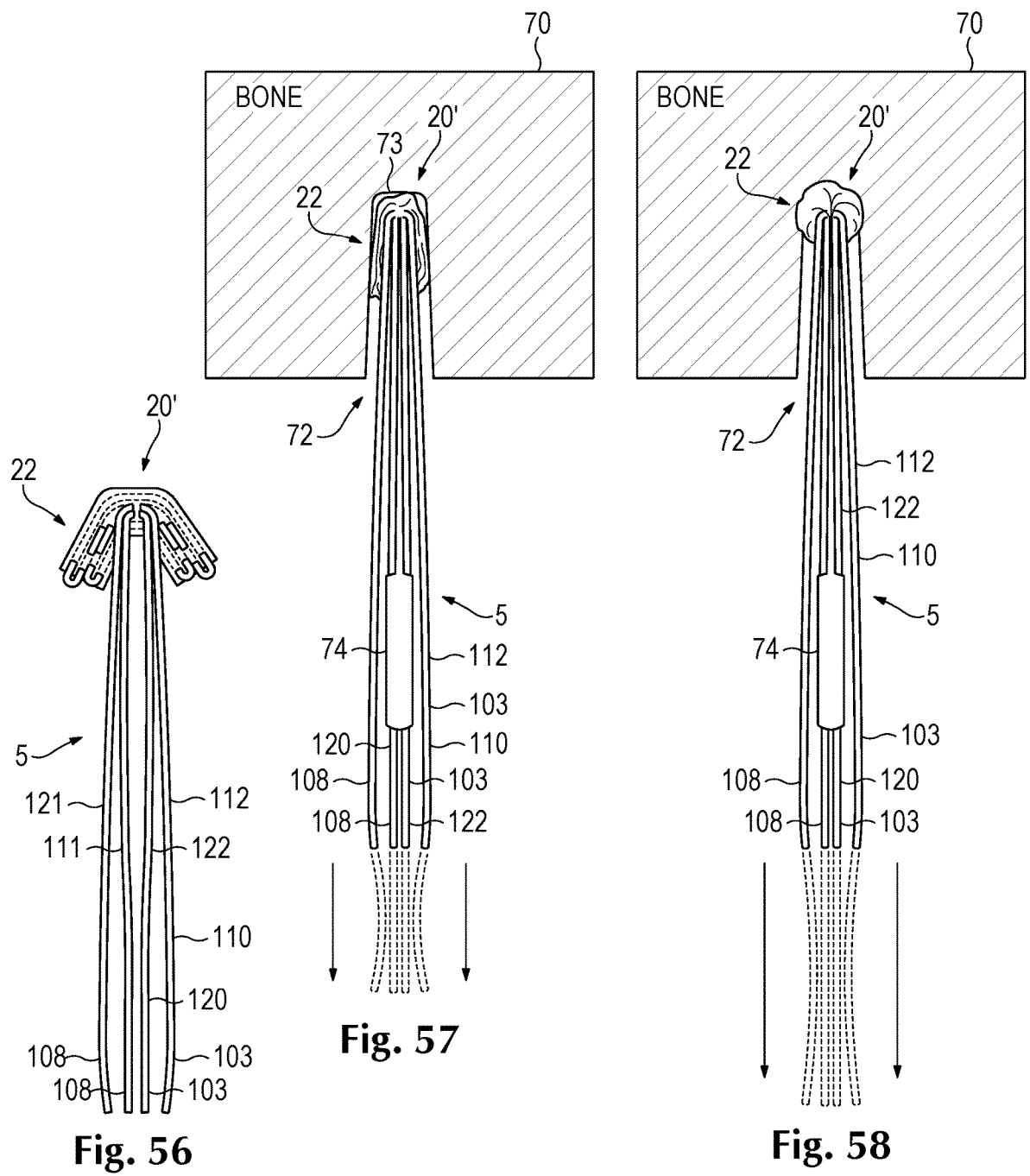

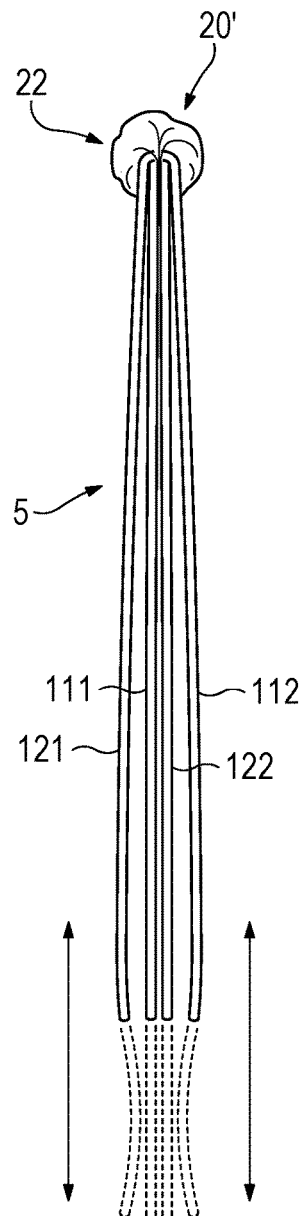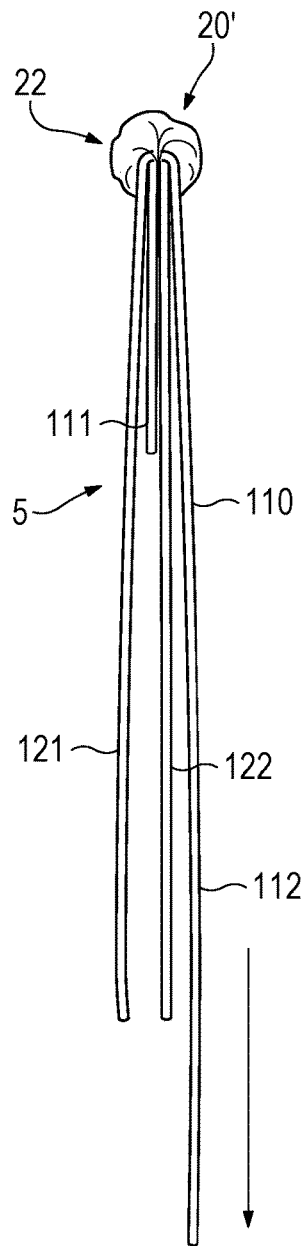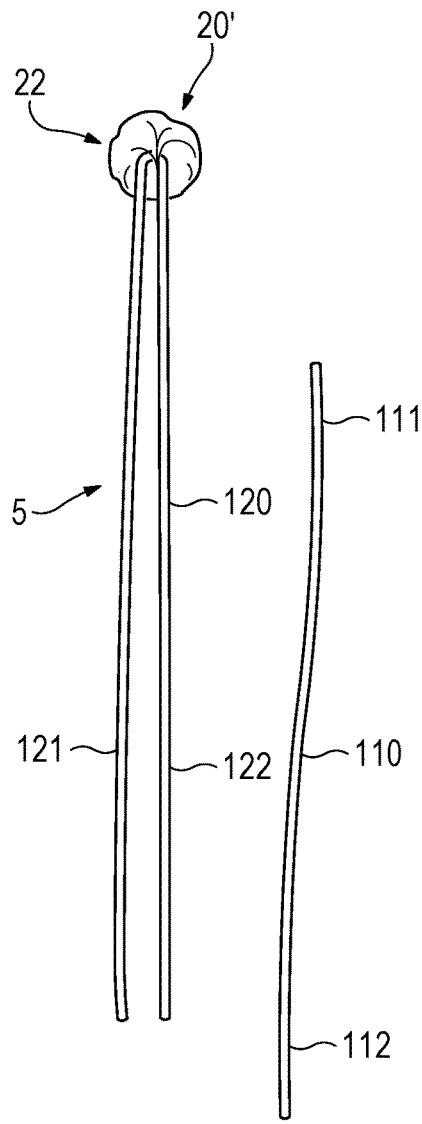
Fig. 59
Fig. 60
Fig. 61

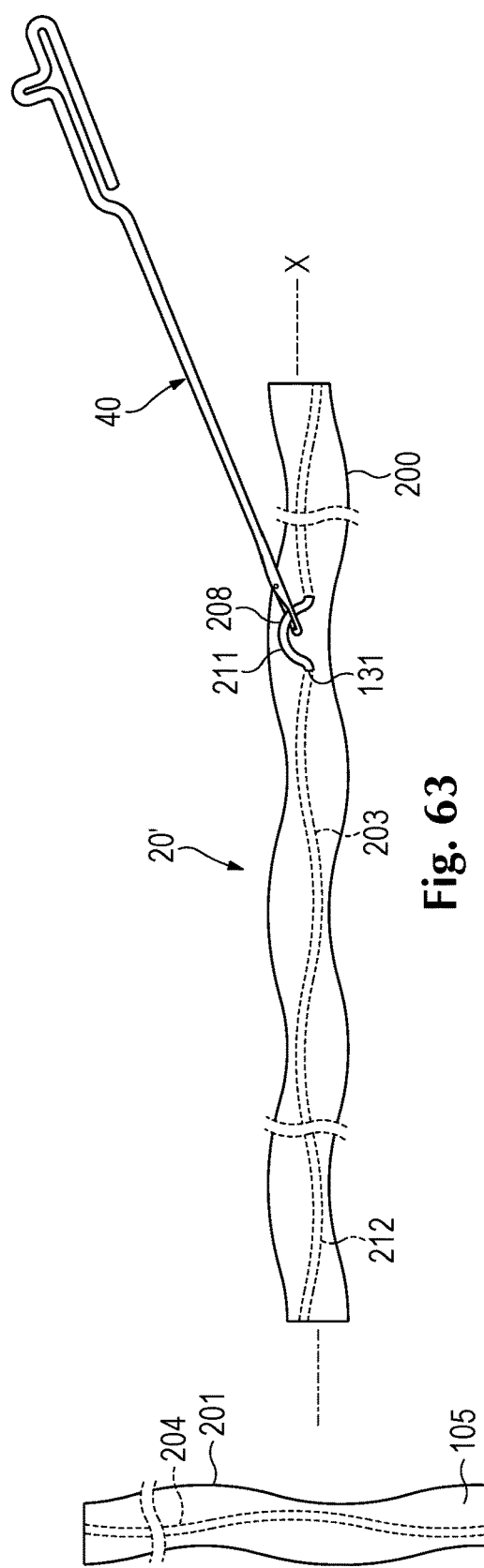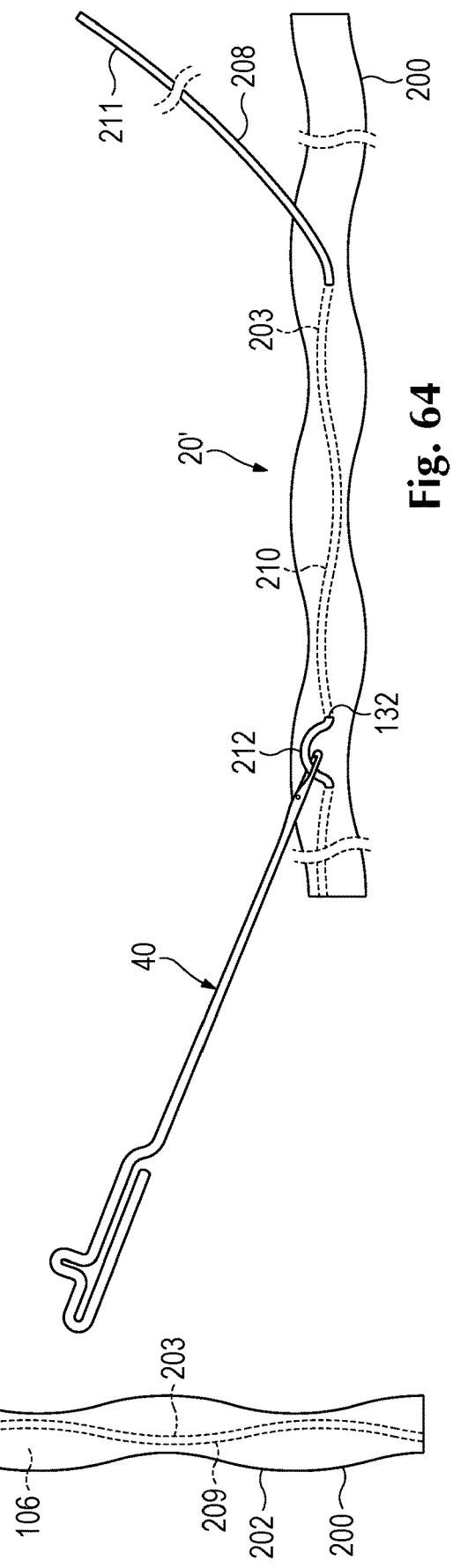

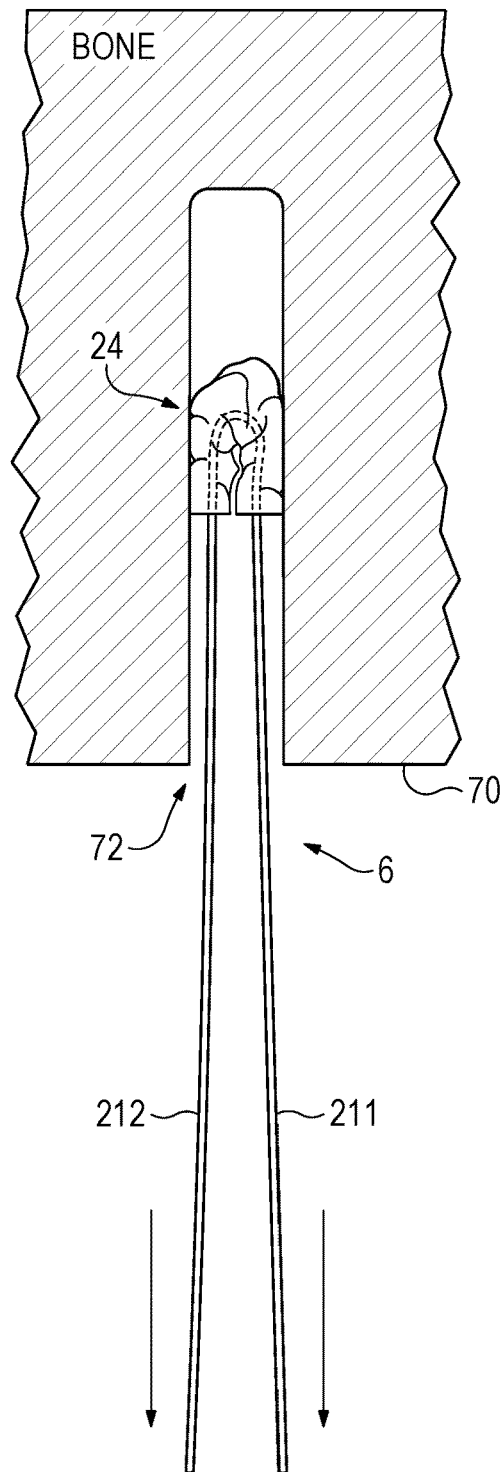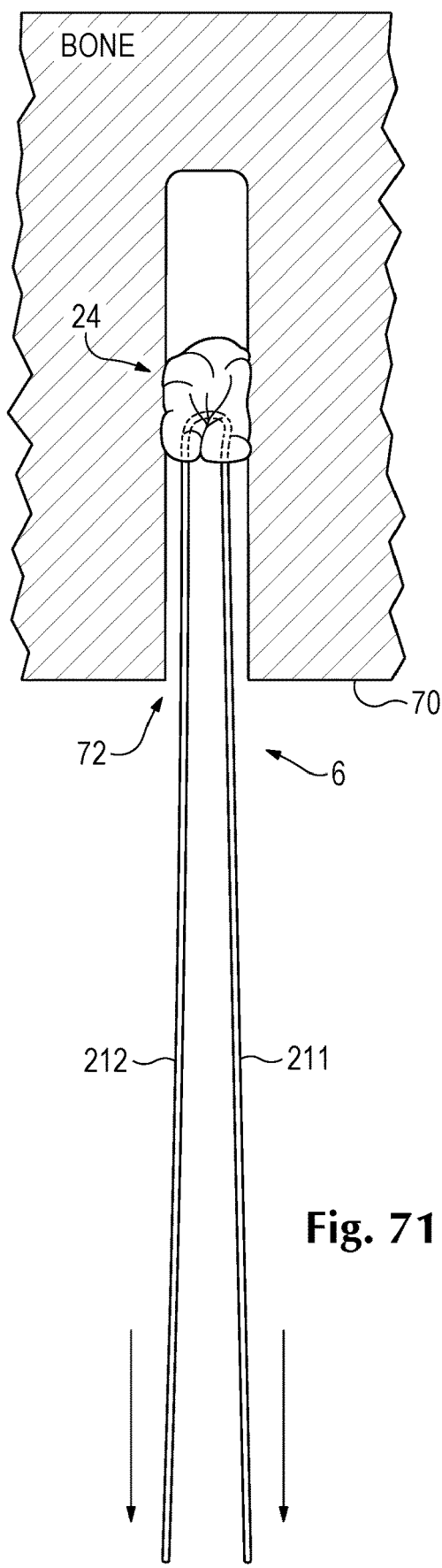
Fig. 70
Fig. 71

SOFT SUTURE ANCHOR

RELATED APPLICATIONS

This application is a continuation-in-part of application U.S. Ser. No. 16/055,464, filed Aug. 6, 2018, which is itself a continuation of patent application U.S. Ser. No. 13/886,126 filed on May 2, 2013, now U.S. Pat. No. 10,070,856 issued on Sep. 11, 2018, which itself claims priority from application Ser. No. 61/642,433, filed on May 3, 2012 and application Ser. No. 61/642,733, filed on May 4, 2012. All of the above noted applications are incorporated by reference as if fully set forth herein.

FIELD

This invention relates to suture systems and more particularly, to soft suture anchors for use in orthopedic surgical techniques.

BACKGROUND

Various orthopedic and other surgical techniques require the use of a suture anchor that engages bone. Common suture anchors are metal screws that have an eyelet at one end. The metal screws are driven into the bone. Suture is passed through the eyelet and is used to bring tissue into contact with the bone for healing. Metal suture anchors pose a number of associated risks, such as, but not limited to, bone fracture, anchor breakage and fragmentation, and anchor dislodgement.

Nonmetallic anchors are known, and typically take the form of soft material that is introduced into a hole that has been drilled into a bone. The anchor is then partially retracted from the hole, and as the result of friction against the side of the hole, bunches up to form a compact anchor as it is retracted, thereby holding to the hole and preventing a complete retraction. Unfortunately, sometimes there is insufficient friction to cause this to happen, and the anchor slips out of the hole, to no effect. Then, the process of attempting to set the anchor must be repeated, driving up time in surgery and possibly necessitating the use of an additional suture anchor.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

In a first separate aspect, the present invention may take the form of a soft anchor construct, having a cross-member suture of braided suture material and a cinching suture that has a first end and a second end. The cinching suture, starting at its first end, extends to the cross-member suture, and engages and traverses the cross-member suture at a first central point and then extends from the first central point to a first lateral point, and engages and traverses the cross-member suture at the first lateral point. The cinching suture then extends from the first lateral point to a second lateral point, opposed to the first lateral point, and engages and traverses the cross-member suture at the second lateral point and then extends from the second lateral point to a second central point and engages and traverses the cross-member suture at the second central point and extends from the second central point to the second end.

In a second separate aspect, the present invention may take the form of a method of anchoring suture to bone, with an anchor set at a target location, comprising, which utilizes an insertion tool sized to enter the pilot hole and having a tip, and a soft anchor construct. The construct includes a cross-member suture, comprising braided suture material, and a cinching suture, having a first end and a second end. The cinching suture extends from the first end to the cross-member suture, and engages and traverses the cross-member suture at a first central point, then further extends from the first central point to a first lateral point, and engages and traverses the cross-member suture at the first lateral point, then further extends from the first lateral point to a second lateral point, opposed to the first lateral point, and engages and traverses the cross-member suture at the second lateral point, then extends from the second lateral point to a second central point and engages and traverses the cross-member suture at the second central point and finally extends from the second central point to the second end. In the method, a pilot hole is created in the bone. The insertion tool tip is used to engage the cross-member suture between the first and second central points and to push the engaged portion of the suture construct to the target location in the pilot hole. Then, while the suture construct is held in place with the insertion tool, pulling on the ends of the cinching suture until the cross-member suture and portions of the cinching suture that are engaged to the cross-member suture cinch up into a ball, thereby setting into the pilot hole at the target location.

In a third separate aspect, the present invention may take the form of a method of producing a soft anchor construct that utilizes a first suture and a second suture, narrower but longer than the first suture. In the method, the second suture is threaded through the first suture, at a first central location, near the midpoint of the first suture length, then the second suture is threaded through the first suture at a first lateral location, between the first central location and a first end of the first suture, then the second suture is threaded through the first suture, at a second lateral location, between the first central location and a second end of the first suture, opposed to the first end of the first suture, finally the second suture is threaded through a second central location, within one fifth of the length of the first suture to the first central location.

In addition to the exemplary aspects and embodiments described above, further aspects and embodiments will become apparent by reference to the drawings and by study of the following detailed descriptions.

BRIEF DESCRIPTION OF THE FIGURES

Exemplary embodiments are illustrated in referenced drawings. It is intended that the embodiments and figures disclosed herein are to be considered illustrative rather than restrictive.

FIG. 1 shows a side view of a suture in accordance with an embodiment;

FIG. 2 shows a side view of the suture of FIG. 1;

FIG. 3 shows a side view of a suture construct in accordance with an embodiment;

FIG. 4 shows a side view of a suture construct in accordance with an embodiment;

FIG. 5 shows a side view of a suture construct in accordance with an embodiment;

FIG. 6 shows a side view of a soft suture anchor in accordance with an embodiment;

FIG. 7 shows a side view of a suture construct in accordance with an embodiment;

FIG. 8 shows a side view of another soft suture anchor in accordance with an embodiment;

FIG. 9 shows a side view of another soft suture anchor in accordance with an embodiment;

FIG. 10 shows a side view of the soft suture anchor in accordance with the embodiment of FIG. 9;

FIG. 13 shows a side view of another suture construct in accordance with an embodiment;

FIG. 14 shows a side view of another suture construct in accordance with an embodiment;

FIG. 15 shows a side view of another soft suture anchor in accordance with an embodiment;

FIG. 16 shows a side view of the soft suture anchor in accordance with the embodiment of FIG. 15;

FIG. 17 shows a side view of the soft suture anchor in accordance with the embodiment of FIG. 15;

FIG. 20 shows a side view of a suture in accordance with an embodiment;

FIG. 21 shows a side view of a suture construct in accordance with an embodiment;

FIG. 22 shows a side view of a suture construct in accordance with an embodiment;

FIG. 23 shows a side view of a suture construct in accordance with an embodiment;

FIG. 24 shows a side view of a suture construct in accordance with an embodiment;

FIG. 25 shows a side view of a suture construct in accordance with an embodiment;

FIG. 26 shows a side view of a suture construct in accordance with an embodiment;

FIG. 27 shows a side view of another soft suture anchor in accordance with an embodiment;

FIG. 28 shows a side view of a suture construct in accordance with an embodiment;

FIG. 29 shows a side view of another soft suture anchor in accordance with an embodiment;

FIG. 30 shows a side view of the soft suture anchor in accordance with the embodiment of FIG. 29;

FIG. 31 shows a side view of the soft suture anchor in accordance with the embodiment of FIG. 29;

FIG. 34 shows a side view of a suture construct in accordance with an embodiment;

FIG. 35 shows a side view of a suture construct in accordance with an embodiment;

FIG. 36 shows a side view of another soft suture anchor in accordance with an embodiment;

FIG. 37 shows a side view of the soft suture anchor in accordance with the embodiment of FIG. 36;

FIG. 38 shows a side view of the soft suture anchor in accordance with the embodiment of FIG. 36;

FIG. 39 shows a side view of the soft suture anchor in accordance with the embodiment of FIG. 36 with the anchor inserted into bone;

FIG. 40 shows a side view of the soft suture anchor in accordance with the embodiment of FIG. 39 anchored into bone;

FIG. 41 shows a side view of suture tape in accordance with an embodiment;

FIG. 42 shows a side view of a suture tape construct in accordance with an embodiment;

FIG. 43 shows a side view of a suture tape construct in accordance with an embodiment;

FIG. 47 shows a side view of a suture tape construct in accordance with an embodiment;

FIG. 48 shows a side view of a suture tape construct in accordance with an embodiment;

FIG. 49 shows a side view of a suture tape construct in accordance with an embodiment;

FIG. 50 shows a side view of a suture tape construct in accordance with an embodiment;

FIG. 51 shows a side view of a suture tape construct in accordance with an embodiment;

FIG. 52 shows a side view of a suture tape construct in accordance with an embodiment;

FIG. 56 shows a side view of the soft suture anchor in accordance with the embodiment of FIG. 54;

FIG. 57 shows a side view of the soft suture anchor in accordance with the embodiment of FIG. 54 with the anchor inserted into bone;

FIG. 58 shows a side view of the soft suture anchor in accordance with the embodiment of FIG. 57 anchored into bone;

FIG. 59 shows a side view of the soft suture anchor in accordance with the embodiment of FIG. 54;

FIG. 60 shows a side view of the soft suture anchor in accordance with the embodiment of FIG. 54;

FIG. 61 shows a side view of the soft suture anchor in accordance with the embodiment of FIG. 54;

FIG. 62 shows a side view of wavy suture tape in accordance with an embodiment;

FIG. 63 shows a side view of a wavy suture tape construct in accordance with an embodiment;

FIG. 64 shows a side view of a wavy suture tape construct in accordance with an embodiment;

FIG. 70 shows a side view of a soft suture anchor in accordance with an embodiment;

FIG. 71 shows a side view of a soft suture anchor in accordance with an embodiment;

DETAILED DESCRIPTION

Figure 11:
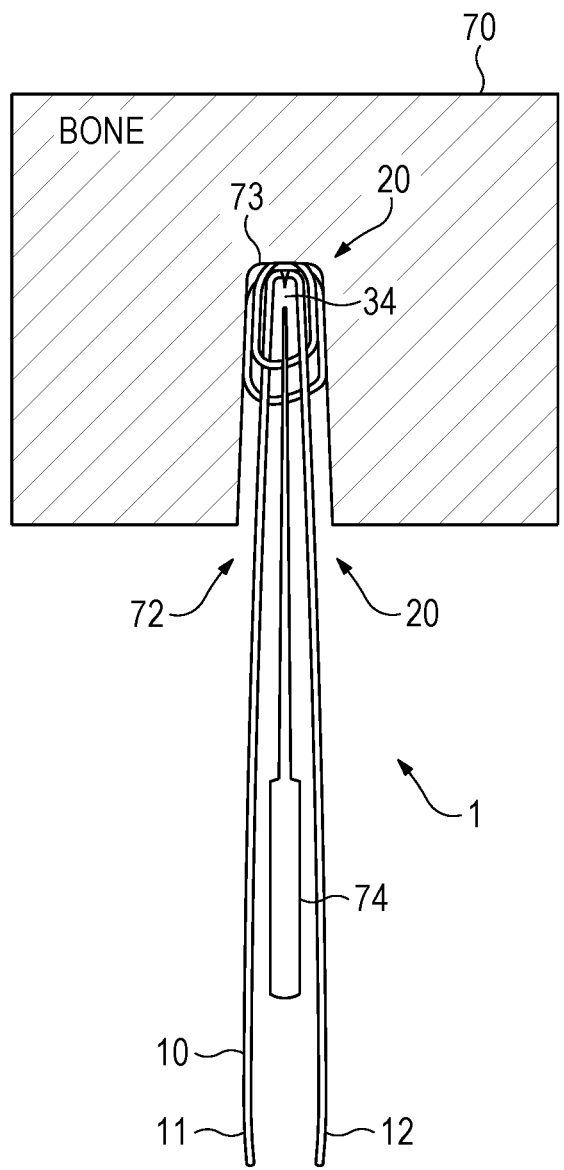
FIG. 11 shows a side view of the soft suture anchor in accordance with the embodiment of FIG. 9 inserted into bone.

References will now be made to embodiments illustrated in the drawings and specific language which will be used to describe the same. It will nevertheless be understood that no limitation of the scope of the invention is thereby intended, such alterations and further modifications in the illustrated devices, as such further applications of the principles of the invention as illustrated therein as being contemplated as would normally occur to one skilled in the art to which the invention relates.

In accordance with embodiments, a soft suture anchor is provided that is made entirely of biocompatible suture material, such as, but not limited to high strength UHMWPE (ultra-high molecular weight polyethylene), polyester, mixtures thereof, and bio-absorbable compounds and mixtures thereof. It is to be understood that any satisfactory material may be used for the soft suture anchor. The use of suture material, as opposed to metal for the anchor, eliminates the possibility of hard loose bodies in the joint and lowers the risk for damage, among other things. It is also understood that the soft suture anchor may comprise a mixture of materials, such as a braid comprising UHMWPE and polyester.

In accordance with embodiments, a soft suture anchor is provided that when deployed, an anchor engages a pilot hole. This ensures firm, reliable fixation throughout the healing period.

As compared with metal suture anchors, the soft suture anchors of embodiments provided herein provide one or more benefits of allowing the use of a smaller pilot hole diameter and depth which allows multiple anchors to be placed in close proximity, reduces the likelihood of intersecting anchors when placing multiple anchors, reduces the possibility of the anchor fracturing the bone, and eliminates use of an anchor that can fracture and cause loose bodies in the joint, among other benefits.

Embodiments of soft suture tape anchors are described below with the suture tape comprising a warp and weft weave configuration. It is appreciated and anticipated herein that other suture tape configurations may be utilized, such as, but not limited to a braid, and therefore, the embodiments are not limited thereto.

Figure 12:
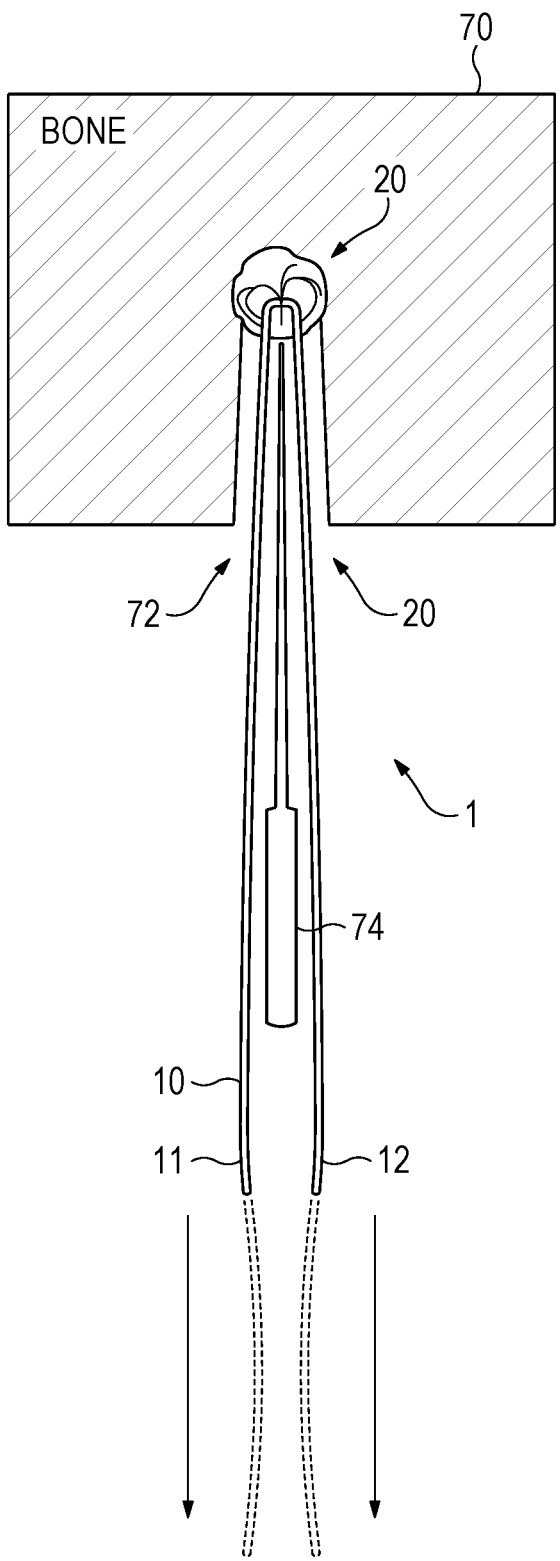
FIG. 12 shows a side view of the soft suture anchor in accordance with the embodiment of FIG. 11 anchored into bone.

FIGS. 9, 11 and 12 are side views of an embodiment of a soft suture anchor 1, comprising an anchor 20 with suture ends 11, 12 extending therefrom. The suture 10 having a tubular braid structure defining a suture wall 13 having a suture outer surface 14 and a lumen 16 therethrough. The suture 10 defines a suture first end 11, a suture second end 12 opposite the suture first end 11, and an anchor 20 between the suture first end 11 and the suture second end 12. The anchor 20 comprises one or more loops 50 formed by extending one or both of the suture first end 11 and suture second end 12 through a first penetration point 31 from the suture outer surface 14 into the lumen 16 and through a second penetration point 32 located a predetermined distance from the first penetration point 31 from the lumen 16 to the suture outer surface 14. The first penetration point 31 and second penetration point 32 are spaced apart and located a predetermined distance from the suture first end 11 and suture second end 12. The first penetration point 31 and the second penetration point 32 define a constrained passageway portion 34 therebetween, wherein causing tension between the passageway portion 34 and the suture first end 11 and the suture second end 12 causes the one or more loops 50 to cinch upon the passageway portion 34 operable to engage a pilot hole 72. Skilled persons will readily recognize, further in view of FIG. 11, that passageway portion 34, both in the embodiment of FIG. 9, but also the embodiments of FIGS. 16 and 27, is also a "hold region," that is, a region that is optimally held in place as ends 11 and 12 are pulled to set anchor 20 into surrounding bone.

Referring to FIG. 1, there is shown a length of suture 1 having a suture first end 11 and a suture second end 12 opposite the suture first end 11. The suture 1 comprises a tubular braid structure defining a suture wall 13 having a suture outer surface 14 and a lumen 16 therethrough. In this embodiment, the suture second end 12 is inserted into the lumen 16 through an aperture in the suture wall 13 so as to extend for a predetermined distance within the lumen 16, and exits the lumen 16 though another aperture in the suture wall 13. Tension placed on the suture first end 11 and suture second end 12 causes a bunching of the suture 1 where the suture first end 11 and suture second end 12 extends for a predetermined distance within the lumen 16 defining an anchor 20. This bunching presenting a large profile so as to wedge the anchor 20 into a pilot hole 72 in bone 70 which is resistant to pull-out. With the anchor 20 coupled into the bone 70, the suture first end 11 and suture second end 12 may be used to engage tissue and hold it against the bone 70 for healing, such as, but not limited to, tendon reattachment.

An embodiment of a method of making a soft suture anchor 1 comprises:

providing a length of suture 10 having a suture first end 11 and a suture second end 12 opposite the suture first end 11, the suture 10 comprising a tubular braid structure defining a suture wall 13 having a suture outer surface 14 and a lumen 16 therethrough, as shown in FIG. 1;

defining a first penetration point 31 and a second penetration point 32 a predetermined distance from the first penetration point 31, the first penetration point 31 and second penetration point 32 are located a predetermined distance from the suture first end 11 and suture second end 12, the first penetration point 31 and the second penetration point 32 defining a passageway portion 34 therebetween, as shown in FIG. 2;

providing a lacing tool 40 comprising an elongated shaft 43 having a shaft first end 41 and a shaft second end 42, a handle 46 optionally formed in the shaft second end 42, the shaft first end 41 formed into a hook 45, the shaft first end 41 further comprising a lever 48 pivotally coupled to the shaft first end 41 adjacent the hook 45 operable to close the hook 45 in a first position and to open the hook 45 in a second position, as shown in FIG. 3;

advancing the hook 45 of the lacing tool 40 from the suture outer surface 14 to the lumen 16 at the first penetration point 31 by advancing the hook 45 through the strands of the braid without breaking the strands;

advancing the hook 45 to the second penetration point 32 within the lumen 16;

advancing the hook 45 from the lumen 16 to the suture outer surface 14 at the second penetration point 32 by advancing the hook 45 through the strands of the braid without breaking the strands, a portion of the shaft 43 extending through the lumen 16 between the first penetration point 31 and the second penetration point 32, as shown in FIG. 3;

placing the suture second end 12 into the hook 45 and closing the lever 48, as shown in FIG. 4; and pulling the hook 45 so as to pull the suture second end 12 into the second penetration point 32, through the lumen 16 and out of the first penetration point 31 forming a loop 50 and removing the lacing tool 40 from the suture 10, wherein the loop 50 and passageway portion 34 define an anchor 20, as shown in FIGS. 5 and 6.

An embodiment of a method for using a soft suture anchor 1 comprises:

placing the anchor 20 into a pilot hole 72 drilled into a bone 70, shown in FIG. 11;

engaging a hold-down tool 74 to hold the anchor 20 at about the base 73 of the pilot hole 72; and putting tension on the suture first end 11 and the suture second end 12 operable to reduce the size of the loop 50 and to cinch the passageway portion 34 operable to engage the pilot hole 72, as shown in FIGS. 11 and 12.

It is appreciated that the method of forming the loop 50 may be repeated so as to form multiple loops. Limiting factors for the number of loops may be the size of the lumen 16 or the size of the penetration holes at the first penetration point 31 and the second penetration point 32.

It is appreciated that the size of the anchor 20 may be dependent on the suture diameter, the number of loops, and the length of the bunching portion.

A longer passageway portion 34 will create a larger anchor profile as compared with a smaller passageway portion 34 wherein the distance between the first penetration point 31 and second penetration point 32 is smaller.

Referring again to FIGS. 1-12, another embodiment is shown comprising a length of suture 10 having a suture first end 11 and a suture second end 12 opposite the suture first end 11. The suture 10 comprises a tubular braid structure defining a suture wall 13 having a suture outer surface 14 and a lumen 16 therethrough. In this embodiment, the suture second end 12 is inserted into the lumen 16 through an aperture in the suture wall 13 so as to extend for a predetermined distance within the lumen 16, and exits the lumen 16 though another aperture in the suture wall 13, as shown in FIGS. 4-6. The suture first end 11 is inserted into the lumen 16 through an aperture in the suture wall 13 so as to extend for a predetermined distance within the lumen 16 of the suture wall 13, and exits the lumen 16 though another aperture in the suture wall 13, as shown in FIGS. 7-8. Tension placed on the suture first end 11 and suture second end 12 causes a bunching of the suture 10 where the suture first end 11 and suture second end 12 extends for a predetermined distance within the lumen 16 defining an anchor 20, this bunching presenting a large profile so as to wedge the anchor 20 into a pilot hole 72 in bone 70 which is resistant to pull-out. With the anchor 20 coupled into the bone 70, the suture first end 11 and suture second end 12 may be used to engage tissue and hold it against the bone 70 for healing, such as, but not limited to, tendon reattachment.

An embodiment of a method of making a soft suture anchor 1 comprises:

providing a length of suture 10 having a suture first end 11 and a suture second end 12 opposite the suture first end 11, the suture 10 comprising a tubular braid structure defining a suture wall 13 having a suture outer surface 14 and a lumen 16 therethrough, as shown in FIG. 1;

defining a first penetration point 31 and a second penetration point 32 a predetermined distance from the first penetration point 31, the first penetration point 31 and second penetration point 32 are located a predetermined distance from the suture first end 11 and the suture second end 12, the first penetration point 31 and the second penetration point 32 defining a passageway portion 34 therebetween, as shown in FIG. 2;

providing a lacing tool 40 comprising an elongated shaft 43 having a shaft first end 41 and a shaft second end 42, a handle 46 optionally formed in the shaft second end 42, the shaft first end 41 defining a hook 45, and a lever 48 pivotally coupled to the shaft first end 41 adjacent the hook 45 operable to close the hook 45 in a first position and to open the hook 45 in a second position;

advancing the hook 45 of the lacing tool 40 from the suture outer surface 14 to the lumen 16 at the first penetration point 31 by advancing the hook 45 through the strands of the braid without breaking the strands;

advancing the hook 45 to the second penetration point 32 within the lumen 16;

advancing the hook 45 from the lumen 16 to the suture outer surface 14 at the second penetration point 32 by advancing the hook 45 through the strands of the braid without breaking the strands, a portion of the shaft 43 extending through the lumen 16 between the first penetration point 31 and the second penetration point 32;

placing the suture second end 12 into the hook 45 and closing the lever 48;

pulling the hook 45 so as to pull the suture second end 12 into the second penetration point 32, through the lumen 16 and out of the first penetration point 31 forming a first loop 51 and removing the lacing tool 40 from the suture 10, as shown in FIGS. 4-6;

advancing the hook 45 of the lacing tool 40 from the suture outer surface 14 to the lumen 16 at the second penetration point 32, as shown in FIG. 7;

advancing the hook 45 to the first penetration point 31 within the lumen 16;

advancing the hook 45 from the lumen 16 to the suture outer surface 14 at the first penetration point 31, a portion of the shaft 43 extending through the lumen 16 between the second penetration point 32 and the first penetration point 31;

placing the suture first end 11 into the hook 45 and closing the lever 48, as shown in FIG. 7; and pulling the hook 45 so as to pull the suture first end 11 into the first penetration point 31, through the lumen 16 and out of the second penetration point 32 forming a second loop 52 and removing the lacing tool 40 from the suture 10, wherein the first loop 51, the second loop 52 and the passageway portion 34 define an anchor 20 as shown in FIGS. 8-10.

It is appreciated that the method of forming the first loop 51 and second loop 52 may be repeated so as to form any number of first loops 51 and second loops 52 suitable for a particular purpose. Limiting factors for the number of first loops 51 and second loops 52 may be the size of the lumen or the size of the penetration holes at the first penetration point and the second penetration point 32.

An embodiment of a method for using a soft suture anchor 1 comprises, as shown in FIGS. 11 and 12:

placing the anchor 20 into a pilot hole 72 drilled into a bone 70, the pilot hole 72 defining a base 73;

engaging a hold-down tool 74 to hold the anchor 20 at about the base 73 of the pilot hole 72; and putting tension on the suture first end 11 and the suture second end 12 operable to reduce the size of the loop 50 and to cinch the passageway portion 34 operable to engage the pilot hole 72.

The hold-down tool 74 is any suitable instrument that is operable to hold the anchor 20 in the pilot hole 72. The hold-down tool 74 may comprise an elongated member with an end that may be received into the pilot hole 72.

Sliding Suture

FIGS. 13-19 are side views of an embodiment of a soft suture anchor 2 including an anchor 20 with suture ends 11, 12 extending therefrom and a sliding suture 80 extending through the anchor 20.

The soft suture anchor 2 comprises:

a sliding suture 80 comprising a length of suture having a sliding suture first end 81 and a sliding suture second end 82 opposite the sliding suture first end 81; and a suture 10 having a tubular braid structure defining a suture wall 13 having a suture outer surface 14 and a lumen 16 therethrough, the suture 10 defining a suture first end 11, a suture second end 12 opposite the suture first end 11, and an anchor 20 between the suture first end 11 and the suture second end 12, the anchor 20 comprising one or more loops formed by extending one or both of the suture first end 11 and suture second end 12 through a first penetration point 31 from the suture outer surface 14 into the lumen 16 and through a second penetration point 32 located a predetermined distance from the first penetration point 31 from the lumen 16 to the suture outer surface 14, the first penetration point 31 and second penetration point 32 being spaced apart and located a predetermined distance from the suture first end 11 and suture second end 12, the first penetration point 31 and the second penetration point 32 defining a passageway portion 34 therebetween, wherein causing tension between the anchor 20 and the suture first end 11 and the suture second end 12 causes the one or more loops to cinch upon the passageway portion 34 operable to engage a pilot hole, wherein the sliding suture 80 extends through the lumen 16 extending from the first penetration point 31 and second penetration point 32, the sliding suture 80 may slide through the anchor 20 along the length of the sliding suture 80.

Figures 18, 19:
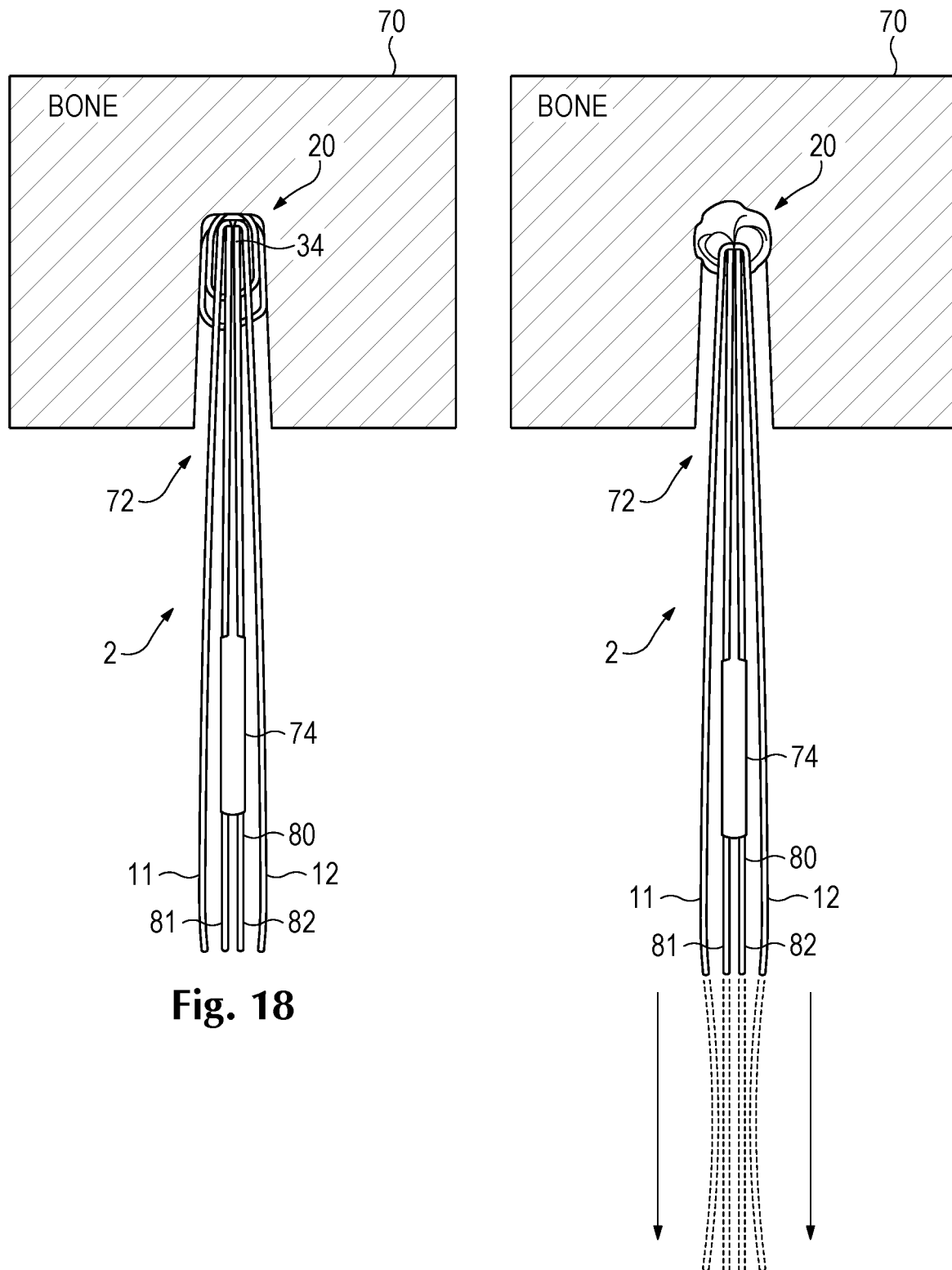
FIG. 18 shows a side view of the soft suture anchor in accordance with the embodiment of FIG. 16 with the anchor inserted into bone.
FIG. 19 shows a side view of the soft suture anchor in accordance with the embodiment of FIG. 18 anchored into bone.

Referring to FIGS. 1-6 and 13-19 are side views of an embodiment of a soft suture anchor 2, a length of suture 1 having a suture first end 11 and a suture second end 12 opposite the suture first end 11. The suture 1 comprises a tubular braid structure defining a suture wall 13 having a suture outer surface 14 and a lumen 16 therethrough, as shown in FIGS. 1-2. In this embodiment, the suture second end 12 is inserted into the lumen 16 through an aperture in the suture wall 13 so as to extend for a predetermined distance within the lumen 16 and exits the lumen 16 though another aperture in the suture wall 13, as shown in FIGS. 3-6. A sliding suture 80 comprising a length of a second suture, is inserted into the lumen 16 through the aperture in the wall of the tubular braid so as to extend for a predetermined distance within the lumen of the tubular braid and exits the lumen though another aperture in the wall of the tubular braid, as shown in FIGS. 13-15. Tension placed on the suture first end 11 and suture second end 12 causes a bunching of the suture 1 where the suture first end 11 and suture second end 12 extends for a predetermined distance within the lumen 16 defining an anchor 20, this bunching presenting a large profile so as to wedge the anchor 20 into a pilot hole 72 in bone 70 which is resistant to pull-out, as shown in FIGS. 18-19. The sliding suture 80 is operable to slide within the anchor 20 along the length of the sliding suture 80. With the anchor 20 coupled into the bone 70, the suture second end 12 and suture second end 12 may be used to engage tissue and hold it against the bone 70 for healing, such as, but not limited to, tendon reattachment.

Referring to FIGS. 1-6 and 13-19, an embodiment of a method of making a soft suture anchor 2 comprises:

providing a length of suture 10 having a suture first end 11 and a suture second end 12 opposite the suture first end 11, the suture 10 comprising a tubular braid structure defining a suture wall 13 having a suture outer surface 14 and a lumen 16 therethrough, as shown in FIGS. 1-2;

defining a first penetration point 31 and a second penetration point 32 a predetermined distance from the first penetration point 31, the first penetration point 31 and second penetration point 32 are located a predetermined distance from the suture first end 11 and suture second end 12, the first penetration point 31 and the second penetration point 32 defining a passageway portion 34 therebetween, as shown in FIG. 3;

providing a lacing tool 40 comprising an elongated shaft 43 having a shaft first end 41 and a shaft second end 42, a handle 46 optionally formed in the shaft second end 42, the shaft first end 41 formed into a hook 45, the shaft first end 41 further comprising a lever 48 pivotally coupled to the shaft first end 41 adjacent the hook 45 operable to close the hook 45 in a first position and to open the hook 45 in a second position, as shown in FIG. 4;

advancing the hook 45 of the lacing tool 40 from the suture outer surface 14 to the lumen 16 at the first penetration point 31 by advancing the hook 45 through the strands of the braid without breaking the strands;

advancing the hook 45 to the second penetration point 32 within the lumen 16;

advancing the hook 45 from the lumen 16 to the suture outer surface 14 at the second penetration point 32 by advancing the hook 45 through the strands of the braid without breaking the strands, a portion of the shaft 43 extending through the lumen 16 between the first penetration point 31 and the second penetration point 32;

placing the suture second end 12 into the hook 45 and closing the lever 48, as shown in FIG. 4;

pulling the hook 45 so as to pull the suture second end 12 into the second penetration point 32, through the lumen 16 and out of the first penetration point 31 forming a loop 50 and removing the lacing tool 40 from the suture 10, wherein the loop and passageway portion 34 define an anchor 20, as shown in FIGS. 5-6;

providing a length of sliding suture 80 having a sliding suture first end 81 and a sliding suture second end 82 opposite the sliding suture first end 81, as shown in FIG. 13;

placing the sliding suture first end 81 into the hook 45 and closing the lever 48, as shown in FIG. 13; and pulling the hook 45 so as to pull the sliding suture first end 81 into the first penetration point 31, through the lumen 16 and out of the second penetration point 32, removing the lacing tool 40 from the suture 10, wherein the sliding suture 80 may slide relative to the anchor 20 along the length of the sliding suture 80, as shown in FIG. 14.

Referring to FIGS. 18-19, an embodiment of a method for using a soft suture anchor 2 comprises:

placing the anchor 20 into a pilot hole 72 drilled into a bone 70 defining a base 73;

engaging a hold-down tool 74 to hold the anchor 20 at about the base 73 of the pilot hole 72, as shown in FIGS. 18-19; and putting tension on the suture first end 11 and the suture second end 12 operable to reduce the size of the loop 50 and to cinch the passageway portion 34 such that the anchor 20 engages the pilot hole 72, wherein the sliding suture 80 may slide through the anchor 20 along the length of the sliding suture 80, as shown in FIG. 19.

It is appreciated that the method of forming the loop 50 may be repeated so as to form multiple loops. Limiting factors for the number of loops may be the size of the lumen 16 or the size of the penetration holes at the first penetration point 31 and the second penetration point 32.

It is appreciated that the size of the anchor 20 may be dependent on the suture diameter, the number of loops, and the length of the bunching portion.

A longer passageway portion 34 will create a larger anchor 20 profile as compared with a smaller passageway portion 34 wherein the distance between the first penetration point 31 and second penetration point 32 is smaller.

The sliding suture 80 may be a monofilament or multifilament twisted or braided suture suitable for a particular purpose. The sliding characteristics of the sliding suture 80 along the length of the sliding suture 80 may be dependent on the surface roughness, compressibility and lubricity, such as from a lubricant, of the sliding suture 80, as well as the tightness of the anchor 20 against the sliding suture 80.

In accordance with another embodiment, referring to FIGS. 1-6 and 13-19, there is shown a length of suture 10 having a suture first end 11 and a suture second end 12 opposite the suture first end 11. The suture 10 comprises a tubular braid structure defining a suture wall 13 having a suture outer surface 14 and a lumen 16 therethrough. In this embodiment, the suture second end 12 is inserted into the lumen 16 through an aperture in the suture wall 13 so as to extend for a predetermined distance within the lumen 16 and exits the lumen 16 though another aperture in the suture wall 13, as shown in FIGS. 3-6. The suture first end 11 is inserted into the lumen 16 through an aperture in the suture wall 13 so as to extend for a predetermined distance within the lumen 16 of the suture 10 and exits the lumen 16 though another aperture in the suture wall 13, as shown in FIGS. 14-15. A sliding suture 80 is inserted into the lumen 16 through the aperture in the suture wall 13 so as to extend for a predetermined distance within the lumen 16 and exits the lumen 16 though another aperture in the suture wall 13, as shown in FIGS. 13-15. Tension placed on the suture first end 11 and suture second end 12 causes a bunching of the suture 10 where the suture first end 11 and suture second end 12 extends for a predetermined distance within the lumen 16 defining an anchor 20, this bunching presenting a profile so as to wedge the anchor 20 into a pilot hole 72 in bone 70 which is resistant to pull-out, as shown in FIGS. 18-19. The sliding suture 80 is operable to slide within the anchor 20 along the length of the sliding suture 80. With the anchor 20 coupled into the bone 70, the suture first end 11 and suture second end 12 may be used to engage tissue and hold it against the bone 70 for healing, such as, but not limited to, tendon reattachment.

Referring to FIGS. 1-6 and 13-19, an embodiment of a method of making a soft suture anchor 2 comprises:

providing a length of suture 10 having a suture first end 11 and a suture second end 12 opposite the suture first end 11, the suture 10 comprising a tubular braid structure defining a suture wall 13 having a suture outer surface 14 and a lumen 16 therethrough, as shown in FIG. 1;

defining a first penetration point 31 and a second penetration point 32 a predetermined distance from the first penetration point 31, the first penetration point 31 and second penetration point 32 are located a predetermined distance from the suture first end 11 and the suture second end 12, the first penetration point 31 and the second penetration point 32 defining a passageway portion 34 therebetween, as shown in FIG. 2;

providing a lacing tool 40 comprising an elongated shaft 43 having a shaft first end 41 and a shaft second end 42, a handle 46 optionally formed in the shaft second end 42, the shaft first end 41 defining a hook 45, and a lever 48 pivotally coupled to the shaft first end 41 adjacent the hook 45 operable to close the hook 45 in a first position and to open the hook 45 in a second position, as shown in FIG. 3;

advancing the hook 45 of the lacing tool 40 from the suture outer surface 14 to the lumen 16 at the first penetration point 31 by advancing the hook 45 through the strands of the braid without breaking the strands;

advancing the hook 45 to the second penetration point 32 within the lumen 16;

advancing the hook 45 from the lumen 16 to the suture outer surface 14 at the second penetration point 32 by advancing the hook 45 through the strands of the braid without breaking the strands, a portion of the shaft 43 extending through the lumen 16 between the first penetration point 31 and the second penetration point 32, as shown in FIG. 3;

placing the suture second end 12 into the hook 45 and closing the lever 48, as shown in FIG. 4;

pulling the hook 45 so as to pull the suture second end 12 into the second penetration point 32, through the lumen 16 and out of the first penetration point 31 forming a first loop 51 and removing the lacing tool 40 from the suture 10, as shown in FIGS. 5-6;

advancing the hook 45 of the lacing tool 40 from the suture outer surface 14 to the lumen 16 at the second penetration point 32;

advancing the hook 45 to the first penetration point 31 within the lumen 16;

advancing the hook 45 from the lumen 16 to the suture outer surface 14 at the first penetration point 31, a portion of the shaft 43 extending through the lumen 16 between the second penetration point 32 and the first penetration point 31, as shown in FIG. 13;

providing a length of sliding suture 80 having a sliding suture first end 81 and a sliding suture second end 82 opposite the sliding suture first end 81, as shown in FIG. 13;

placing the sliding suture first end 81 into the hook 45 and closing the lever 48, as shown in FIG. 14;

pulling the hook 45 so as to pull the sliding suture first end 81 into the first penetration point 31, through the lumen 16 and out of the second penetration point 32 removing the lacing tool 40 from the suture 10, as shown in FIG. 14;

advancing the hook 45 of the lacing tool 40 from the suture outer surface 14 to the lumen 16 at the second penetration point 32;

advancing the hook 45 to the first penetration point 31 within the lumen 16;

advancing the hook 45 from the lumen 16 to the suture outer surface 14 at the first penetration point 31, a portion of the shaft 43 extending through the lumen 16 between the second penetration point 32 and the first penetration point 31;

placing the suture first end 11 into the hook 45 and closing the lever 48, as shown in FIG. 14; and pulling the hook 45 so as to pull the suture first end 11 into the first penetration point 31, through the lumen 16 and out of the second penetration point 32 forming a second loop 52 and removing the lacing tool 40 from the suture 10, wherein the first loop 51, the second loop 52 and the passageway portion 34 define an anchor 20, wherein the sliding suture 80 may slide relative to the anchor 20 along the length of the sliding suture 80, as shown in FIGS. 15-17.

It is appreciated that the method of forming the first loop 51 and second loop 52 may be repeated so as to form any number of first loops 51 and second loops 52 suitable for a particular purpose. Limiting factors for the number of first loops 51 and second loops 52 may be the size of the lumen or the size of the penetration holes at the first penetration point and the second penetration point 32.

Referring to FIGS. 18-19, an embodiment of a method for using a soft suture anchor 2 comprises:

placing the anchor 20 into a pilot hole 72 drilled into a bone 70, the pilot hole 72 defining a base 73, as shown in FIG. 18;

engaging a hold-down tool 74 to hold the anchor 20 at about the base 73 of the pilot hole 72, as shown in FIG. 18; and putting tension on the suture first end 11 and the suture second end 12 operable to reduce the size of the loop 50 and to cinch the passageway portion 34 such that the anchor 20 engages the pilot hole 72, wherein the sliding suture 80 may slide through the anchor 20 along the length of the sliding suture 80, as shown in FIG. 19.

The hold-down tool 74 is any suitable instrument that is operable to hold the anchor 20 in the pilot hole 72. The hold-down tool 74 may comprise an elongated member with an end that may be received into the pilot hole 72.

It is appreciated that the method of forming the first loop 51 and second loop 52 may be repeated so as to form any number of first loops 51 and second loops 52 suitable for a particular purpose. Limiting factors for the number of first loops 51 and second loops 52 may be the size of the lumen or the size of the penetration holes at the first penetration point 31 and the second penetration point 32.

The sliding suture 80 may be a monofilament or multifilament twisted or braided suture suitable for a particular purpose. The sliding characteristics of the sliding suture relative to the anchor 20 may be dependent on the surface roughness, compressibility and lubricity, such as from a lubricant, of the sliding suture 80, as well as the tightness of the anchor 20 against the sliding suture 80.

Bulking Suture

The size of the anchor 20 may be further increased by the inclusion of a bulking suture 90, that is, an additional length of suture that is substantially the same or smaller in length as the passageway portion 34 between the first penetration point 31 and a second penetration point 32. The bulking suture 90 includes a bulking suture first end 91 and a bulking suture second end 92 opposite the bulking suture first end 91. The bulking suture 90 comprises a tubular structure defining a bulking suture lumen 93 therethrough.

FIGS. 30-33 are side views of an embodiment of a soft suture anchor 3 including an anchor 20 with bulking suture 90, and suture ends 11, 12 extending from the anchor 20.

Referring to FIGS. 20-33, an embodiment of a method of making a soft suture anchor 3, comprising:

a bulking suture 90 comprising a length of suture having a bulking suture first end 91 and a bulking suture second end 92 opposite the bulking suture first end 91, the bulking suture 90 comprising a tubular structure defining a bulking suture lumen 93 therethrough, as shown in FIG. 21; and a suture 10 having a tubular braid structure defining a suture wall 13 having a suture outer surface 14 and a lumen 16 therethrough, the suture 10 defining a suture first end 11, a suture second end 12 opposite the suture first end 11, and an anchor 20 between the suture first end 11 and the suture second end 12, the anchor 20 comprising one or more loops formed by extending one or both of the suture first end 11 and suture second end 12 through a first penetration point 31 from the suture outer surface 14 into the lumen 16 and through a second penetration point 32 located a predetermined distance from the first penetration point 31 from the lumen 16 to the suture outer surface 14, the first penetration point 31 and second penetration point 32 being spaced apart and located a predetermined distance from the suture first end 11 and suture second end 12, the first penetration point 31 and the second penetration point 32 defining a passageway portion 34 therebetween, as shown in FIGS. 20-27, wherein the bulking suture 90 has a length that is substantially the same or smaller as the passageway portion 34, wherein the passageway portion 34 extends within the bulking suture lumen, as shown in FIG. 23, wherein causing tension between the anchor 20 and the suture first end 11 and the suture second end 12 causes the one or more loops 50 to cinch upon the passageway portion 34 and the bulking suture 90 operable to engage a pilot hole 72, as shown in FIGS. 30-33.

Referring to FIGS. 20-33, there is shown a length of suture 10 having a suture first end 11 and a suture second end 12 opposite the suture first end 11. The suture 10 comprises a tubular braid structure defining a suture wall 13 having a suture outer surface 14 and a lumen 16 therethrough, as shown in FIG. 20. In this embodiment, a second suture, called a bulking suture 90, is placed over a portion of the suture 10, as shown in FIGS. 21-22. The suture second end 12 is inserted into the lumen 16 through an aperture in the suture wall 13 adjacent a bulking suture first end 91 of the bulking suture 90 so as to extend for a predetermined distance within the lumen 16 and exits the lumen 16 though another aperture in the suture wall 13 adjacent a bulking suture second end 92 of the bulking suture 90, as shown in FIGS. 23-27. Tension placed on the suture first end 11 and suture second end 12 causes a bunching of the suture 10 where the suture first end 11 and suture second end 12 extends for a predetermined distance within the lumen 16 and about the bulking suture 90 defining an anchor 20, this bunching presenting a large profile so as to wedge the anchor 20 into a pilot hole 72 in bone 70 which is resistant to pull-out, as shown in FIGS. 30-33. With the anchor 20 coupled into the bone 70, the suture first end 11 and suture second end 12 may be used to engage tissue and hold it against the bone 70 for healing, such as, but not limited to, tendon reattachment.

Referring to FIGS. 20-33, an embodiment of a method of making a soft suture anchor 3 comprises:

providing a length of suture 10 having a suture first end 11 and a suture second end 12 opposite the suture first end 11, the suture 10 comprising a tubular braid structure defining a suture wall 13 having a suture outer surface 14 and a lumen 16 therethrough, as shown in FIG. 20;

defining a first penetration point 31 and a second penetration point 32 a predetermined distance from the first penetration point 31, the first penetration point 31 and second penetration point 32 are located a predetermined distance from the suture first end 11 and suture second end 12, the first penetration point 31 and the second penetration point 32 defining a passageway portion 34 therebetween, as shown in FIG. 23;

providing a lacing tool 40 comprising an elongated shaft 43 having a shaft first end 41 and a shaft second end 42, a handle 46 optionally formed in the shaft second end 42, the shaft first end 41 formed into a hook 45, the shaft first end 41 further comprising a lever 48 pivotally coupled to the shaft first end 41 adjacent the hook 45 operable to close the hook 45 in a first position and to open the hook 45 in a second position, as shown in FIG. 21;

providing a length of bulking suture 90 that is substantially the same or smaller in length as the passageway portion 34 between the first penetration point 31 and a second penetration point 32, the bulking suture 90 including a bulking suture first end 91 and a bulking suture second end 92 opposite the bulking suture first end 91, the bulking suture 90 comprising a tubular structure defining a bulking suture lumen therethrough, as shown in FIG. 21;

threading the suture second end 12 through the bulking suture lumen 93 and advancing the bulking suture 90 to the passageway portion 34, as shown in FIG. 22;

in another embodiment, threading comprises: advancing the hook 45 of the lacing tool 40 through the bulking suture lumen 94 such that the bulking suture is disposed on the shaft of the lacing tool 40 between the hook 45 and the handle; placing the suture second end 12 into the hook 45 and closing the lever 48; and pulling the hook 45 so as to pull the suture second end 12 into and through the bulking suture lumen and removing the lacing tool 40 from the bulking suture lumen, as shown in FIG. 21;

advancing the hook 45 of the lacing tool 40 from the suture outer surface 14 to the lumen 16 at the first penetration point 31 by advancing the hook 45 through the strands of the braid without breaking the strands;

advancing the hook 45 to the second penetration point 32 within the lumen 16;

advancing the hook 45 from the lumen 16 to the suture outer surface 14 at the second penetration point 32 by advancing the hook 45 through the strands of the braid without breaking the strands, a portion of the shaft 43 extending through the lumen 16 between the first penetration point 31 and the second penetration point 32, as shown in FIG. 24;

placing the suture second end 12 into the hook 45 and closing the lever 48, as shown in FIG. 25;

pulling the hook 45 so as to pull the suture second end 12 into the second penetration point 32, through the lumen 16 and out of the first penetration point 31 forming a loop 50 and removing the lacing tool 40 from the suture 10, wherein the loop 50, the bulking suture 90 and the passageway portion 34 define an anchor 20, as shown in FIGS. 26-27.

Figures 32, 33:
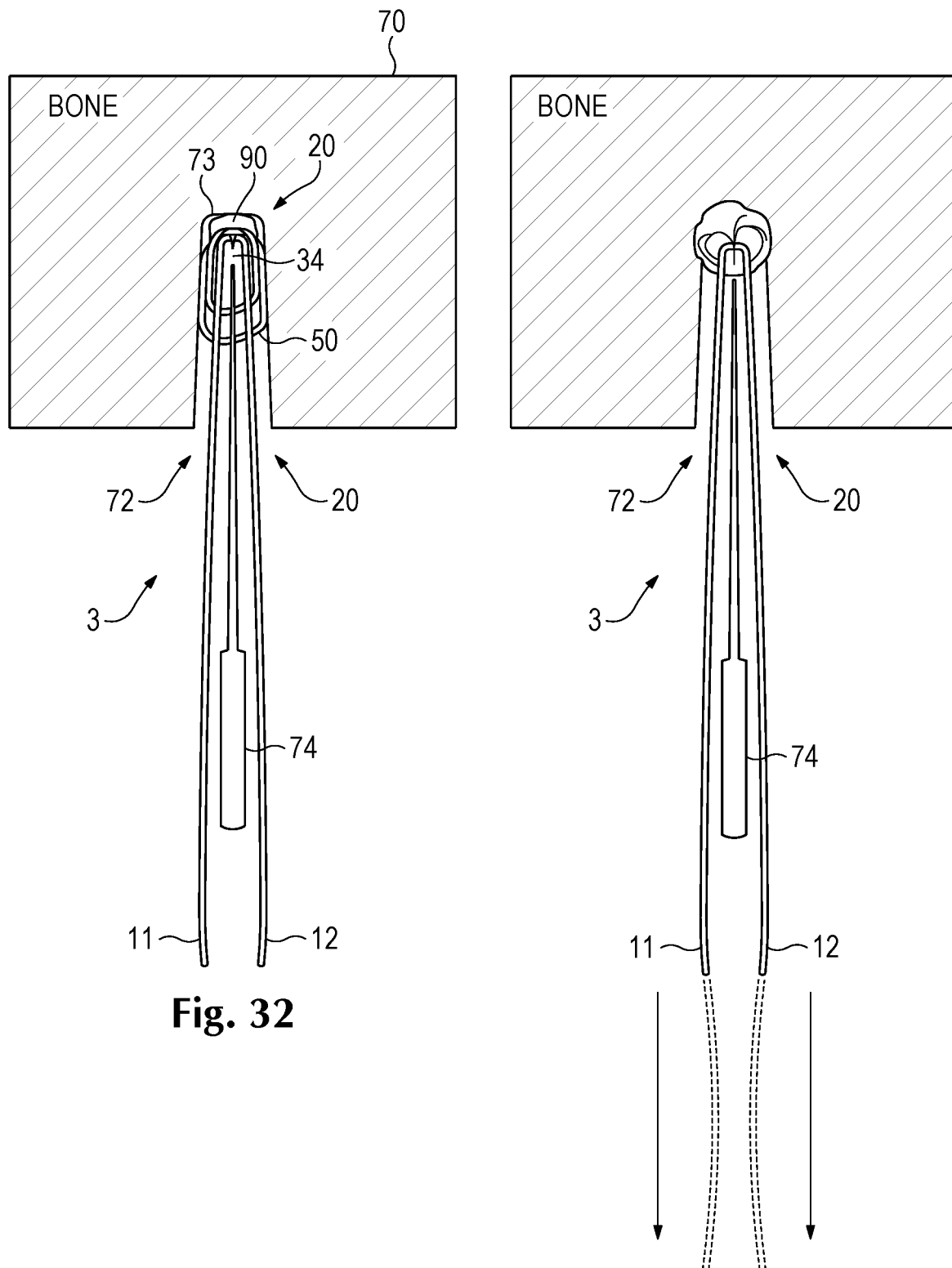
FIG. 32 shows a side view of the soft suture anchor in accordance with the embodiment of FIG. 29 with the anchor inserted into bone.
FIG. 33 shows a side view of the soft suture anchor in accordance with the embodiment of FIG. 32 anchored into bone.

Referring to FIGS. 32-33, an embodiment of a method for using a soft suture anchor 3 comprises:

placing the anchor 20 into a pilot hole 72 drilled into a bone 70, as shown in FIG. 32;

engaging a hold-down tool 74 to hold the anchor 20 at about the base 73 of the pilot hole 72, as shown in FIG. 32; and putting tension on the suture first end 11 and the suture second end 12 operable to reduce the size of the loop 50 and to cinch the passageway portion 34 and bulking suture 90 such that the anchor 20 engages the pilot hole 72, as shown in FIG. 33.

The hold-down tool 74 is any suitable instrument that is operable to hold the anchor 20 in the pilot hole 72. The hold-down tool 74 may comprise an elongated member with an end that may be received into the pilot hole 72.

It is appreciated that the method of forming the loop 50 may be repeated so as to form multiple loops. Limiting factors for the number of loops may be the size of the lumen 16 or the size of the penetration holes at the first penetration point 31 and the second penetration point 32.

It is appreciated that the size of the anchor 20 may be dependent on the suture diameter, the number of loops, and the length of the bunching portion, and the length, size and thickness of the bulking suture 90, among other things.

A longer passageway portion 34 will create a larger anchor profile as compared with a smaller passageway portion 34 wherein the distance between the first penetration point 31 and second penetration point 32 is smaller.

A longer or thicker bulking suture 90 will create a larger anchor profile as compared with a shorter or thinner bulking suture 90.

Referring to FIGS. 20-33, there is shown a length of suture 10 having a suture first end 11 and a suture second end 12 opposite the suture first end 11. The suture 10 comprises a tubular braid structure defining a suture wall 13 having a suture outer surface 14 and a lumen 16 therethrough, as shown in FIG. 20.

In this embodiment, a second suture, called a bulking suture 90, is placed over a portion of the suture 10, as shown in FIG. 22. the suture second end 12 is inserted into the lumen 16 through an aperture in the suture wall 13 adjacent a bulking suture first end 91 of the bulking suture 90 so as to extend for a predetermined distance within the lumen 16 and exits the lumen 16 though another aperture in the suture wall 13 adjacent a bulking suture second end 92 of the bulking suture 90, as shown in FIG. 27. The suture first end 11 is inserted into the lumen 16 through an aperture in the suture wall 13 so as to extend for a predetermined distance within the lumen 16 of the suture wall 13 and exits the lumen 16 though another aperture in the suture wall 13, as shown in FIGS. 28-29. Tension placed on the suture first end 11 and suture second end 12 causes a bunching of the suture 10 where the suture first end 11 and suture second end 12 extends for a predetermined distance within the lumen 16 and about the bulking suture defining an anchor 20, this bunching presenting a large profile so as to wedge the anchor 20 into a pilot hole 72 in bone 70 which is resistant to pull-out, as shown in FIGS. 32-33. With the anchor 20 coupled into the bone 70, the suture first end 11 and suture second end 12 may be used to engage tissue and hold it against the bone 70 for healing, such as, but not limited to, tendon reattachment.

Referring to FIGS. 20-33, an embodiment of a method of making a soft suture anchor 3 comprises:

providing a length of suture 10 having a suture first end 11 and a suture second end 12 opposite the suture first end 11, the suture 10 comprising a tubular braid structure defining a suture wall 13 having a suture outer surface 14 and a lumen 16 therethrough, as shown in FIG. 20;

defining a first penetration point 31 and a second penetration point 32 a predetermined distance from the first penetration point 31 on the suture 10, the first penetration point 31 and second penetration point 32 are located a predetermined distance from the suture first end 11 and suture second end 12, the first penetration point 31 and the second penetration point 32 defining a passageway portion 34 therebetween, as shown in FIGS. 23-24;

providing a lacing tool 40 comprising an elongated shaft 43 having a shaft first end 41 and a shaft second end 42, a handle 46 optionally formed in the shaft second end 42, the shaft first end 41 formed into a hook 45, the shaft first end 41 further comprising a lever 48 pivotally coupled to the shaft first end 41 adjacent the hook 45 operable to close the hook 45 in a first position and to open the hook 45 in a second position, as shown in FIG. 24;

providing a length of bulking suture 90 that is substantially the same or smaller in length as the passageway portion 34 between the first penetration point 31 and a second penetration point 32, the bulking suture 90 including a bulking suture first end 91 and a bulking suture second end 92 opposite the bulking suture first end 91, the bulking suture 90 comprising a tubular structure defining a bulking suture lumen 93 therethrough, as shown in FIGS. 22-23;

threading the suture second end 12 through the bulking suture lumen 93 and advancing the bulking suture 90 to the passageway portion 34, as shown in FIG. 22;

in another embodiment, threading comprises: advancing the hook 45 of the lacing tool 40 through the bulking suture lumen 93 such that the bulking suture 90 is disposed on the shaft of the lacing tool 40 between the hook 45 and the handle; placing the suture second end 12 into the hook 45 and closing the lever 48; and pulling the hook 45 so as to pull the suture second end 12 into and through the bulking suture lumen and removing the lacing tool 40 from the bulking suture lumen, as shown in FIGS. 21-22;

advancing the hook 45 of the lacing tool 40 from the suture outer surface 14 to the lumen 16 at the first penetration point 31 by advancing the hook 45 through the strands of the braid without breaking the strands;

advancing the hook 45 to the second penetration point 32 within the lumen 16;

advancing the hook 45 from the lumen 16 to the suture outer surface 14 at the second penetration point 32 by advancing the hook 45 through the strands of the braid without breaking the strands, a portion of the shaft 43 extending through the lumen 16 between the first penetration point 31 and the second penetration point 32, as shown in FIG. 24;

placing the suture second end 12 into the hook 45 and closing the lever 48, as shown in FIG. 25;

pulling the hook 45 so as to pull the suture second end 12 into the second penetration point 32, through the lumen 16 and out of the first penetration point 31 forming a loop 50 and removing the lacing tool 40 from the suture 10, as shown in FIGS. 26-27;

advancing the hook 45 of the lacing tool 40 from the suture outer surface 14 to the lumen 16 at the second penetration point 32;

advancing the hook 45 to the first penetration point 31 within the lumen 16;

advancing the hook 45 from the lumen 16 to the suture outer surface 14 at the first penetration point 31, a portion of the shaft 43 extending through the lumen 16 between the second penetration point 32 and the first penetration point 31;

placing the suture first end 11 into the hook 45 and closing the lever 48, as shown in FIG. 28; and pulling the hook 45 so as to pull the suture first end 11 into the first penetration point 31, through the lumen 16 and out of the second penetration point 32 forming a second loop 52 and removing the lacing tool 40 from the suture 10, wherein the first loop 51, the second loop 52, the passageway portion 34, and the bulking suture 90 define an anchor 20, as shown in FIG. 29-31.

Referring to FIGS. 32-33, an embodiment of a method for using a soft suture anchor 3 comprises:

placing the anchor 20 into a pilot hole 72 drilled into a bone 70, as shown in FIG. 32;

engaging a hold-down tool 74 to hold the anchor 20 at about the base 73 of the pilot hole 72, as shown in FIG. 32; and putting tension on the suture first end 11 and the suture second end 12 operable to reduce the size of the loop 50 and the second loop 52 to cinch the passageway portion 34 and bulking suture 90 operable to engage the pilot hole 72, as shown in FIG. 33.

The hold-down tool 74 is any suitable instrument that is operable to hold the anchor 20 in the pilot hole 72. The hold-down tool 74 may comprise an elongated member with an end that may be received into the pilot hole 72.

It is appreciated that the method of forming the first loop 51 and the second loop 52 may be repeated so as to form multiple loops. Limiting factors for the number of loops may be the size of the lumen 16 or the size of the penetration holes at the first penetration point 31 and the second penetration point 32.

It is appreciated that the size of the anchor may be dependent on the suture diameter, the number of loops, and the length of the bunching portion, and the length, size and thickness of the bulking suture 90, among other things.

A longer passageway portion 34 will create a larger anchor profile as compared with a smaller passageway portion 34 wherein the distance between the first penetration point 31 and second penetration point 32 is smaller.

A longer or thicker bulking suture 90 will create a larger anchor profile as compared with a shorter or thinner bulking suture 90.

FIGS. 37-40 are side views of an embodiment of a soft suture anchor 4 including an anchor 20 with a bulking suture 90, with suture ends 11, 12 extending from the anchor 20, and a sliding suture 80 extending through the anchor 20.

Referring to FIGS. 20-27 and 34-40, a soft suture anchor 4, comprising, a sliding suture 80 comprising a length of suture having a sliding suture first end 81 and a sliding suture second end 82 opposite the sliding suture first end 81;

a bulking suture 90 comprising a length of suture having a bulking suture first end 91 and a bulking suture second end 92 opposite the bulking suture first end 91, the bulking suture 90 comprising a tubular structure defining a bulking suture lumen 93 therethrough; and a suture 10 having a tubular braid structure defining a suture wall 13 having a suture outer surface 14 and a lumen 16 therethrough, the suture 10 defining a suture first end 11, a suture second end 12 opposite the suture first end 11, and an anchor 20 between the suture first end 11 and the suture second end 12, the anchor 20 comprising one or more loops formed by extending one or both of the suture first end 11 and suture second end 12 through a first penetration point 31 from the suture outer surface 14 into the lumen 16 and through a second penetration point 32 located a predetermined distance from the first penetration point 31 from the lumen 16 to the suture outer surface 14, the first penetration point 31 and second penetration point 32 being spaced apart and located a predetermined distance from the suture first end 11 and suture second end 12, the first penetration point 31 and the second penetration point 32 defining a passageway portion 34 therebetween, wherein the bulking suture has a length that is substantially the same or smaller as the passageway portion 34, wherein the passageway portion 34 extends within the bulking suture lumen 93, wherein the passageway portion 34, the one or more loops, and the bulking suture 90 define an anchor 20, wherein the sliding suture 80 extends through the lumen 16 extending from the first penetration point 31 and second penetration point 32, wherein causing tension between the anchor 20 and the suture first end 11 and the suture second end 12 causes the one or more loops to cinch upon the passageway portion 34 and the bulking suture 90 operable to engage a pilot hole 72, wherein the sliding suture 80 may slide through the anchor 20 along the length of the sliding suture 80.

Referring to FIGS. 20-27 and 34-40, there is shown a length of suture 4 having a suture first end 11 and a suture second end 12 opposite the suture first end 11. The suture 10 comprises a tubular braid structure defining a suture wall 13 having a suture outer surface 14 and a lumen 16 therethrough, as shown in FIG. 20.

A bulking suture 90 is placed over a portion of the suture 10, as shown in FIG. 22. The suture second end 12 is inserted into the lumen 16 through an aperture in the suture wall 13 adjacent a bulking suture first end 91 of the bulking suture 90 so as to extend for a predetermined distance within the lumen 16, and exits the lumen 16 though another aperture in the suture wall 13 adjacent a bulking suture second end 92 of the bulking suture 90, as shown in FIGS. 24-27. A sliding suture 80 comprising a length of a second suture, is inserted into the lumen 16 through the aperture in the suture wall 13 of the suture 10 so as to extend for a predetermined distance within the lumen 16 of the suture 10 and exits the lumen 16 though another aperture in the suture wall 13 of the suture 10, as shown in FIGS. 34-36. Tension placed on the suture first end 11 and suture second end 12 causes a bunching of the suture 4 where the suture first end 11 and suture second end 12 extends for a predetermined distance within the lumen 16 and about the bulking suture defining an anchor 20, this bunching presenting a large profile so as to wedge the anchor 20 into a pilot hole 72 in bone 70 which is resistant to pull-out. The sliding suture 80 is operable to slide within the anchor 20 along the length of the sliding suture 80. With the anchor 20 coupled into the bone 70, the suture first end 11 and suture second end 12 may be used to engage tissue and hold it against the bone 70 for healing, such as, but not limited to, tendon reattachment, as shown in FIGS. 37-40.

Referring to FIGS. 20-27 and 34-40, an embodiment of a method of making a soft suture anchor 4 comprises:

providing a length of suture 10 having a suture first end 11 and a suture second end 12 opposite the suture first end 11, the suture 10 comprising a tubular braid structure defining a suture wall 13 having a suture outer surface 14 and a lumen 16 therethrough, as shown in FIG. 20;

defining a first penetration point 31 and a second penetration point 32 a predetermined distance from the first penetration point 31, the first penetration point 31 and second penetration point 32 are located a predetermined distance from the suture first end 11 and suture second end 12, the first penetration point 31 and the second penetration point 32 defining a passageway portion 34 therebetween, as shown in FIG. 34;

providing a lacing tool 40 comprising an elongated shaft 43 having a shaft first end 41 and a shaft second end 42, a handle 46 optionally formed in the shaft second end 42, the shaft first end 41 formed into a hook 45, the shaft first end 41 further comprising a lever 48 pivotally coupled to the shaft first end 41 adjacent the hook 45 operable to close the hook 45 in a first position and to open the hook 45 in a second position, as shown in FIG. 21;

providing a length of bulking suture that is substantially the same or smaller in length as the passageway portion 34 between the first penetration point and a second penetration point 32, the bulking suture including a bulking suture first end 91 and a bulking suture second end 92 opposite the bulking suture first end 91, the bulking suture comprising a tubular structure defining a bulking suture lumen therethrough, as shown in FIG. 21;

threading the suture second end 12 through the bulking suture lumen and advancing the bulking suture to the passageway portion 34, as shown in FIG. 22;

in another embodiment, threading comprises: advancing the hook 45 of the lacing tool 40 through the bulking suture lumen such that the bulking suture is disposed on the shaft of the lacing tool 40 between the hook 45 and the handle; placing the suture second end 12 into the hook 45 and closing the lever 48; and pulling the hook 45 so as to pull the suture second end 12 into and through the bulking suture lumen and removing the lacing tool 40 from the bulking suture lumen, as shown in FIG. 21;

advancing the hook 45 of the lacing tool 40 from the suture outer surface 14 to the lumen 16 at the first penetration point 31 by advancing the hook 45 through the strands of the braid without breaking the strands;

advancing the hook 45 to the second penetration point 32 within the lumen 16;

advancing the hook 45 from the lumen 16 to the suture outer surface 14 at the second penetration point 32 by advancing the hook 45 through the strands of the braid without breaking the strands, a portion of the shaft 43 extending through the lumen 16 between the first penetration point 31 and the second penetration point 32, as shown in FIG. 24;

placing the suture second end 12 into the hook 45 and closing the lever 48, as shown in FIG. 25;

pulling the hook 45 so as to pull the suture second end 12 into the second penetration point 32, through the lumen 16 and out of the first penetration point 31 forming a loop 50 and removing the lacing tool 40 from the suture 10, wherein the loop 50, the bulking suture 90, and the passageway portion 34 define an anchor 20, as shown in FIG. 26-27;

providing a length of sliding suture 80 having a sliding suture first end 81 and a sliding suture second end 82 opposite the sliding suture first end 81, as shown in FIG. 34;

placing the sliding suture first end 81 into the hook 45 and closing the lever 48, as shown in FIG. 34; and pulling the hook 45 so as to pull the sliding suture first end 81 into the first penetration point 31, through the lumen 16 and out of the second penetration point 32, removing the lacing tool 40 from the suture 10, wherein the sliding suture 80 may slide relative to the anchor 20 along the length of the sliding suture 80, as shown in FIG. 35.

Referring to FIGS. 39-40, an embodiment of a method for using a soft suture anchor 4 comprises:

placing the anchor 20 into a pilot hole 72 drilled into a bone 70 defining a base 73, as shown in FIG. 39;

engaging a hold-down tool 74 to hold the anchor 20 at about the base 73 of the pilot hole 72, as shown in FIG. 39; and putting tension on the suture first end 11 and the suture second end 12 operable to reduce the size of the loop 50 and to cinch the bulking suture 90 and the passageway portion 34 operable to engage the pilot hole 72, wherein the sliding suture may slide through the anchor 20 along the length of the sliding suture 80, as shown in FIG. 40.

The hold-down tool 74 is any suitable instrument that is operable to hold the anchor 20 in the pilot hole 72. The hold-down tool 74 may comprise an elongated member with an end that may be received into the pilot hole 72.

It is appreciated that the method of forming the loop 50 may be repeated so as to form multiple loops. Limiting factors for the number of loops may be the size of the lumen 16 or the size of the penetration holes at the first penetration point 31 and the second penetration point 32.

It is appreciated that the size of the anchor may be dependent on the suture diameter, the number of loops, and the length of the bunching portion.

A longer passageway portion 34 will create a larger anchor profile as compared with a smaller passageway portion 34 wherein the distance between the first penetration point 31 and second penetration point 32 is smaller.

The sliding suture 80 may be a monofilament or multifilament twisted or braided suture suitable for a particular purpose. The sliding characteristics of the sliding suture 80 along the length of the sliding suture 80 may be dependent on the surface roughness, compressibility and lubricity, such as from a lubricant, of the sliding suture 80, as well as the tightness of the anchor 20 against the sliding suture 80.

Referring to FIGS. 20-27 and 34-40, there is shown a length of suture 10 having a suture first end 11 and a suture second end 12 opposite the suture first end 11. The suture 10 comprises a tubular braid structure defining a suture wall 13 having a suture outer surface 14 and a lumen 16 therethrough, as shown in FIG. 20.

A bulking suture 90 is placed over a portion of the suture 10, as shown in FIG. 22. The suture second end 12 is inserted into the lumen 16 through an aperture in the suture wall 13 adjacent a bulking suture first end 91 of the bulking suture 90 so as to extend for a predetermined distance within the lumen 16, and exits the lumen 16 though another aperture in the suture wall 13 adjacent a bulking suture second end 92 of the bulking suture 90, as shown in FIGS. 24-27. The suture first end 11 is inserted into the lumen 16 through an aperture in the suture wall 13 so as to extend for a predetermined distance within the lumen 16 of the suture 10 and exits the lumen 16 though another aperture in the suture wall 13, as shown in FIG. 35-36. A sliding suture 80 comprising a length of a second suture, is inserted into the lumen 16 through the aperture in the suture wall 13 of the suture 10 so as to extend for a predetermined distance within the lumen 16 of the suture 10 and exits the lumen 16 though another aperture in the suture wall 13 of the suture 10, as shown in FIGS. 34-35. Tension placed on the suture first end 11 and suture second end 12 causes a bunching of the suture 1 where the suture first end 11 and suture second end 12 extends for a predetermined distance within the lumen 16 and about the bulking suture defining an anchor 20, this bunching presenting a large profile so as to wedge the anchor 20 into a pilot hole 72 in bone 70 which is resistant to pull-out, as shown in FIGS. 37-40. The sliding suture 80 is operable to slide within the anchor 20 along the length of the sliding suture 80. With the anchor 20 coupled into the bone 70, the suture first end 11 and suture second end 12 may be used to engage tissue and hold it against the bone 70 for healing, such as, but not limited to, tendon reattachment.

Referring to FIGS. 20-27 and 34-40, an embodiment of a method of making a soft suture anchor 4 comprises:

providing a length of suture 10 having a suture first end 11 and a suture second end 12 opposite the suture first end 11, the suture 10 comprising a tubular braid structure defining a suture wall 13 having a suture outer surface 14 and a lumen 16 therethrough, as shown in FIG. 20;

defining a first penetration point 31 and a second penetration point 32 a predetermined distance from the first penetration point 31, the first penetration point 31 and second penetration point 32 are located a predetermined distance from the suture first end 11 and suture second end 12, the first penetration point 31 and the second penetration point 32 defining a passageway portion 34 therebetween, as shown in FIG. 23;

providing a lacing tool 40 comprising an elongated shaft 43 having a shaft first end 41 and a shaft second end 42, a handle 46 optionally formed in the shaft second end 42, the shaft first end 41 formed into a hook 45, the shaft first end 41 further comprising a lever 48 pivotally coupled to the shaft first end 41 adjacent the hook 45 operable to close the hook 45 in a first position and to open the hook 45 in a second position, as shown in FIG. 21;

providing a length of bulking suture that is substantially the same or smaller in length as the passageway portion 34 between the first penetration point and a second penetration point 32, the bulking suture including a bulking suture first end 91 and a bulking suture second end 92 opposite the bulking suture first end 91, the bulking suture 90 comprising a tubular structure defining a bulking suture lumen therethrough, as shown in FIG. 21;

threading the suture second end 12 through the bulking suture lumen and advancing the bulking suture to the passageway portion 34, as shown in FIG. 22;

in another embodiment, threading comprises: advancing the hook 45 of the lacing tool 40 through the bulking suture lumen such that the bulking suture is disposed on the shaft of the lacing tool 40 between the hook 45 and the handle; placing the suture second end 12 into the hook 45 and closing the lever 48; and pulling the hook 45 so as to pull the suture second end 12 into and through the bulking suture lumen and removing the lacing tool 40 from the bulking suture lumen, as shown in FIG. 21;

advancing the hook 45 of the lacing tool 40 from the suture outer surface 14 to the lumen 16 at the first penetration point 31 by advancing the hook 45 through the strands of the braid without breaking the strands;

advancing the hook 45 to the second penetration point 32 within the lumen 16;

advancing the hook 45 from the lumen 16 to the suture outer surface 14 at the second penetration point 32 by advancing the hook 45 through the strands of the braid without breaking the strands, a portion of the shaft 43 extending through the lumen 16 between the first penetration point 31 and the second penetration point 32, as shown in FIG. 24;

placing the suture second end 12 into the hook 45 and closing the lever 48, as shown in FIG. 25;

pulling the hook 45 so as to pull the suture second end 12 into the second penetration point 32, through the lumen 16 and out of the first penetration point 31 forming a first loop 51 and removing the lacing tool 40 from the suture 10, as shown in FIG. 26-27;

advancing the hook 45 of the lacing tool 40 from the suture outer surface 14 to the lumen 16 at the second penetration point 32;

advancing the hook 45 to the first penetration point 31 within the lumen 16;

advancing the hook 45 from the lumen 16 to the suture outer surface 14 at the first penetration point 31, a portion of the shaft 43 extending through the lumen 16 between the second penetration point 32 and the first penetration point 31, as shown in FIG. 28;

placing the suture first end 11 into the hook 45 and closing the lever 48, as shown in FIG. 28; and pulling the hook 45 so as to pull the suture first end 11 into the first penetration point 31, through the lumen 16 and out of the second penetration point 32 forming a second loop 52 and removing the lacing tool 40 from the suture 10, wherein the first loop 51, the second loop 52 and the passageway portion 34 define an anchor 20, advancing the hook 45 of the lacing tool 40 from the suture outer surface 14 to the lumen 16 at the first penetration point 31 by advancing the hook 45 through the strands of the braid without breaking the strands, as shown in FIG. 29;

advancing the hook 45 through the second penetration point 32 and within the lumen 16;

advancing the hook 45 from the lumen 16 to the suture outer surface 14 at the first penetration point 31 by advancing the hook 45 through the strands of the braid without breaking the strands, a portion of the shaft 43 extending through the lumen 16 between the second penetration point 32 and the first penetration point 31, as shown in FIG. 34;

providing a length of sliding suture 80 having a sliding suture first end 81 and a sliding suture second end 82 opposite the sliding suture first end 81, as shown in FIG. 34;

placing the sliding suture first end 81 into the hook 45 and closing the lever 48, as shown in FIG. 35; and pulling the hook 45 so as to pull the sliding suture first end 81 into the first penetration point 31, through the lumen 16 and out of the second penetration point 32, removing the lacing tool 40 from the suture 10, wherein the sliding suture 80 may slide relative to the anchor 20 along the length of the sliding suture 80, as shown in FIG. 35 36.

Referring to FIGS. 39-40, an embodiment of a method for using a soft suture anchor 4 comprises: placing the anchor 20 into a pilot hole 72 drilled into a bone 70 defining a base 73, as shown in FIG. 39; engaging a hold-down tool 74 to hold the anchor 20 at about the base 73 of the pilot hole 72, as shown in FIG. 39; and putting tension on the suture first end 11 and the suture second end 12 operable to reduce the size of the first loop 51 and the second loop 52 and to cinch the bulking suture 90 and the passageway portion 34 operable to engage the pilot hole 72, wherein the sliding suture 80 may slide through the anchor 20 along the length of the sliding suture 80, as shown in FIG. 40.

The hold-down tool 74 is any suitable instrument that is operable to hold the anchor 20 in the pilot hole 72. The hold-down tool 74 may comprise an elongated member with an end that may be received into the pilot hole 72.

It is appreciated that the method of forming the first loop 51 and second loop 52 may be repeated so as to form any number of first loops 51 and second loops 52 suitable for a particular purpose. Limiting factors for the number of first loops 51 and second loops 52 may be the size of the lumen 16 or the size of the penetration holes at the first penetration point and the second penetration point 32.

It is appreciated that the size of the anchor may be dependent on the suture diameter, the number of loops, the length of the bunching portion and the length, size and thickness of the bulking suture 90, among other things.

A longer passageway portion 34 will create a larger anchor profile as compared with a smaller passageway portion 34 wherein the distance between the first penetration point 31 and second penetration point 32 is smaller.

A longer or thicker bulking suture 90 will create a larger anchor profile as compared with a shorter or thinner bulking suture 90.

The sliding suture 80 may be a monofilament or multifilament twisted or braided suture suitable for a particular purpose. The sliding characteristics of the sliding suture 80 along the length of the sliding suture 80 may be dependent on the surface roughness, compressibility and lubricity, such as from a lubricant, of the sliding suture 80, as well as the tightness of the anchor 20 against the sliding suture 80.

In accordance with an embodiment, the soft suture anchor comprises a suture having a tubular braid construction defining a lumen therethrough. The suture defines a suture first end, a suture second end opposite the suture first end, and an anchor between the suture first end and the suture second end. The anchor comprises the suture configured into one or more loops wherein causing tension between the anchor and the suture first end and the suture second end causes the one or more loops to cinch and present a profile operable to wedge the anchor into a pilot hole which is resistant to pull-out.

In another embodiment, the soft suture anchor further comprises at least a portion of each of the one or more loops extends within the lumen at a bunching portion. The bunching portion is that portion of the suture between wherein the one or more loops enters the lumen and exits the lumen, wherein causing tension between the anchor and the suture first end and the suture second end causes the one or more loops to cinch and bunch the bunching portion so as to present a profile operable to wedge the anchor into a pilot hole which is resistant to pull-out.

In another embodiment, the soft suture anchor further comprises a second suture having a tubular braid construction defining a second lumen therethrough, the second suture advanced over the suture via the second lumen and positioned at the bunching portion, wherein causing tension between the anchor and the suture first end and the suture second end causes the one or more loops to cinch and bunch the bunching portion and second suture so as to present a profile operable to wedge the anchor into a pilot hole which is resistant to pull-out.

In another embodiment, the soft suture anchor further comprises a third suture, the third suture advanced through the lumen at the bunching portion, wherein causing tension between the anchor and the suture first end and the suture second end causes the one or more loops to cinch and bunch the bunching portion so as to present a profile operable to wedge the anchor into a pilot hole which is resistant to pull-out while allowing the third suture to slide relative to the anchor.

In other embodiments, the soft suture anchor further comprises combinations of the elements described above.

Per the requirements of the application, the suture can be composed of any suitable material which can be processed to prepare a filamentary strand. For example, the suture may be composed of an absorbable or nonabsorbable material, and it can be configured as a braid, or if desired, as a monofilament. An example of a nonabsorbable material is polyester and UHMWPE. Examples of absorbable materials are derived from homopolymers and copolymers of glycolide, lactide, ε-caprolactone, p-dioxanone, and trimethylene, polybutylene succinate, polycaprolatone (PCL), polyglycolic acid (PGA), and polylactic acid (PLA). Bio absorbable sutures may be used in procedures, such as, but not limited to, that require temporary fixation of tissue to bone during the healing process but is not required after healing.

The soft suture anchors 1, 2, 3, 4 provided in embodiments above may be provided to the physician in kit form with various sutures 10 and a lacing tool 40 where the physician may make an anchor 20 of a particular size and configuration suitable for a particular purpose.

The soft suture anchor may be provided to the physician in its assembled form and in various anchor sizes.

The soft suture anchor may be provided to the physician mounted to a hold-down rod used to insert and hold the anchor at the base of the pilot hole during insertion and deployment.

A lacing tool 40 is described above as having a lever 48 that is pivotally coupled to the shaft and opens the hook-shaped distal portion in a first position and closes the hook shaped distal portion in a second position. In an alternative embodiment, the leaver is replaced by a latch that is slidably coupled to the shaft and may be advanced away from the hook-shaped distal portion in a first position to open, and advanced over the hook-shaped distal portion in a second position to close. It is appreciated that there are many tools which may provide the functionality of the lacing tool 40 as described, and the examples provided above are non-limiting.

By way of example of the use of embodiments of soft suture anchors provided herein, a Bankart repair is discussed below. It is understood that this is only an example and the use of the soft suture anchors is not to be limited thereto.

For treatment of a Bankart lesion wherein there is detachment of the inferior half of the anterior glenoid labrum, embodiments of the soft suture anchors provided herein replace the metal bone suture anchors and sutures commonly used for this procedure.

Once the glenoid rim has been prepared, three pilot holes are made on the glenoid rim at the osteochondral junction, or just on the joint surface. These drill holes will each accommodate one of the soft suture anchors provided herein. The soft suture anchors should be distributed along the glenoid rim to allow the entire detached capsule to be securely fixed to bone. The lower anchor should be introduced as low as possible, and the remaining two about 1 to 1.5 cm apart.

The anchor is placed into the pilot holes that were drilled into the bone. A tool is used to hold the anchor at about the base of the pilot hole while simultaneous tension is made on the suture first end and suture second end operable to cinch the bunching portion so as to cause the anchor to present a profile so as to wedge the anchor into the pilot hole which is resistant to pull-out.

One of the suture first end and suture second end is taken inside out through the medial rim of the detached capsule of labral tissue. This distal placement of the sutures in the capsule allows a slight proximal shift of the capsule during the repair in cases with inferior laxity. With all three sutures passed through the capsule, a trial reduction can be carried out. The surgeon reduces the capsule onto the glenoid rim by tying the other of the suture first end and suture second end to the respective other suture, thus repairing the anterior capsule onto the glenoid rim. The two strands from adjacent anchors are tied together. By tying single strands of sutures from adjacent anchors together, a strong horizontal mattress suture line is created on the glenoid rim holding the capsule firmly down onto the bone. The knots are completed, thus completely obliterating the glenoid rim defect and, if desired, shifting the inferior capsule proximally (or in a cephalad direction).

The soft suture anchor provided in embodiments above may be used in many surgical procedures, including, but not limited to: Shoulders—Labral repair and rotator cuff repair; Foot and ankle—Medial/lateral repair and reconstruction, Mid-and forefoot repair, Hallux valgus reconstruction, Metatarsal ligament/tendon repair or reconstruction, and Achilles Tendon Repair; and Hand and Wrist Indications—Collateral ligament repair, Scapholunate ligament reconstruction, tendon transfers in phalanx, and Volar plate reconstruction.

Suture Tape Anchor

FIGS. 55-58 are side views of an embodiment of a soft suture tape anchor assembly 5 including a deployed anchor 22 with suture ends 111, 112, 121, 122 extending therefrom.

Referring to FIGS. 41-61, a soft suture tape anchor assembly 5 comprises a length of suture tape 100 having a suture tape first end 101 and a suture tape second end 102 opposite the suture tape first end 101, as shown in FIG. 41. The suture tape 100 comprises a weave including a plurality of warp suture strands 103 woven in a warp configuration (where the strands are substantially parallel to the longitudinal central axis X) and weft suture strands (not shown, where the strands are substantially perpendicular to the longitudinal axis X) woven in a weft configuration. The ends of one or more warp suture strands 103 are deconstructed from the weave of the suture tape 100, and hereinafter referred to as deconstructed suture strands 108, leaving an alternative variant of an anchor in the form of a woven anchor 20' (FIGS. 45 and 46), of the warp suture strands 103 remaining in the weave, as shown in FIGS. 42 46. The deconstructed suture strands 108 comprise a deconstructed suture strand first end 104 and a deconstructed suture strand second end 109 opposite from the deconstructed suture strand first end 104. The deconstructed suture strand first end 104 and the deconstructed suture strand second end 109 of the one or more deconstructed suture strands 108 being rewoven in retrograde (opposite direction of the original direction of the strand) direction into the anchor 20' to emerge from a center location 140 of the anchor or anchor 20', as shown in FIGS. 47-55, operable such that tension on the deconstructed suture strand first end 104 and the deconstructed suture strand second end 109 of the one or more deconstructed suture strands 108 causes the anchor 20' to cinch and/or bunch together and present a profile such that the deployed anchor 22 engages a pilot hole 72 in bone 70 which is resistant to pullout.

In accordance with embodiments, the suture tape 100 is made entirely of biocompatible suture material, such as, but not limited to UHMWPE (ultra-high molecular weight polyethylene), polyester, mixtures thereof, and bio absorbable compounds and mixtures such as, but not limited to polybutylene succinate, polycaprolatone (PCL), polyglycolic acid (PGA), and polylactic acid (PLA).

In accordance with an embodiment, one or more of the warp strands may be UHMWPE with the remainder being polyester, by way of example. In accordance with an embodiment, one or more individual suture strands may be woven in the warp orientation and used as the suture strands that extend from the anchor, in a secondary process after the production of a suture tape. In accordance with an embodiment, one or more individual UHMWPE strands may be weaved in the warp orientation and used as the suture strands that extend from the anchor, in a secondary process after the production of a suture tape.

Referring to FIGS. 41-61, there is shown a length of suture tape 100 having a suture tape first end 101 and a suture tape second end 102 opposite the suture tape first end 101, as shown in FIG. 41. The suture tape 100 comprises a plurality of suture strands 103 woven in a warp and weft configuration defining a weave. In this embodiment, the ends of one or more warp suture strands 103 are deconstructed from the weave of the suture tape 100, and hereinafter referred to as deconstructed suture strands 108, defining an anchor 20' comprising a portion of the warp suture strands remaining in the weave, as shown in FIGS. 42-46. The deconstructed suture strands 108 comprise a deconstructed suture strand first end 104 and a deconstructed suture strand second end 109 opposite from the deconstructed suture strand first end 104. The deconstructed suture strand first end 104 and the deconstructed suture strand second end 109 are subsequently rewoven in retrograde direction into the anchor 20' to emerge from a center location 140 of the anchor 20', as shown in FIG. 47-55. The anchor 20' may be disposed in a pilot hole 72, such as a pilot hole 72 resulting from drilling into bone 70, as shown in FIG. 57. Tension on the deconstructed suture strand first end 104 and the deconstructed suture strand second end 109 causes the anchor 20' to cinch and/or bunch together and present a profile so as to wedge the deployed anchor 22 into the pilot hole 72 which is resistant to pull-out, as shown in FIG. 58. With the deployed anchor 22 anchored into the bone 70, the deconstructed suture strand first end 104 and the deconstructed suture strand second end 109 may be used to engage tissue and hold it against the bone 70 for, such as, but not limited to, tendon reattachment.

Figure 44:
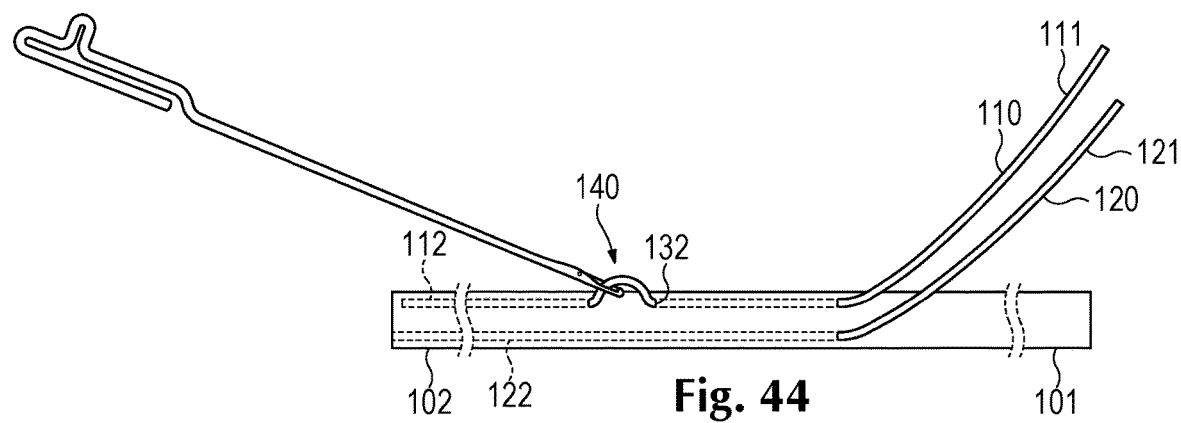
FIG. 44 shows a side view of a suture tape construct in accordance with an embodiment.
Figure 45:
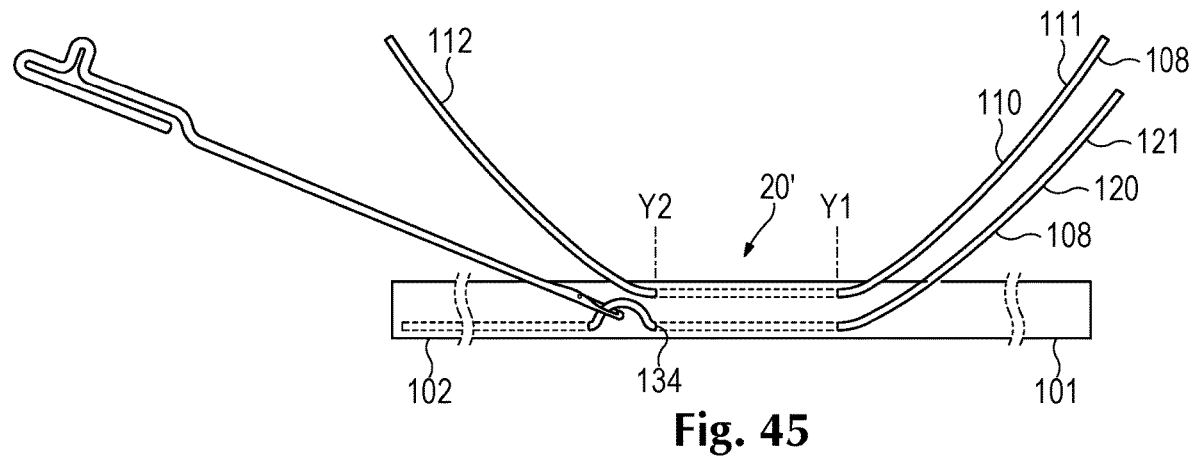
FIG. 45 shows a side view of a suture tape construct in accordance with an embodiment.
Figure 46:
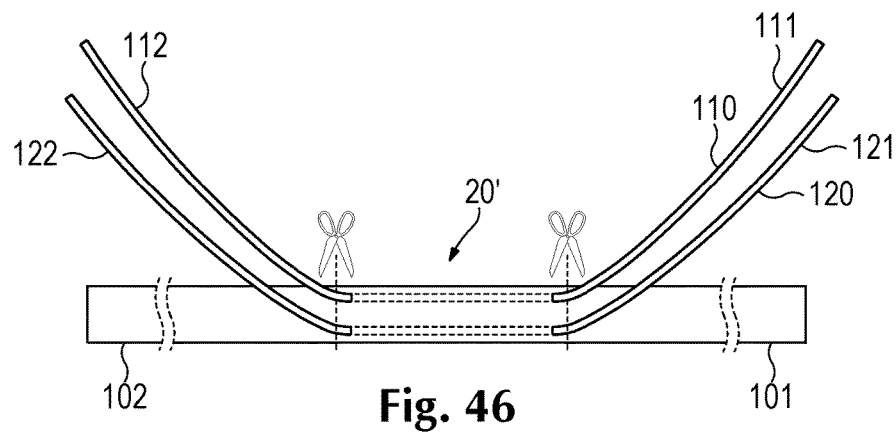
FIG. 46 shows a side view of a suture tape construct in accordance with an embodiment.
Figure 53:
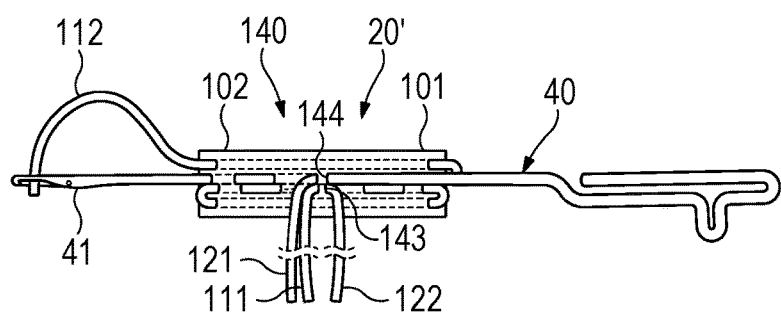
FIG. 53 shows a side view of a suture tape construct in accordance with an embodiment.
Figure 54:
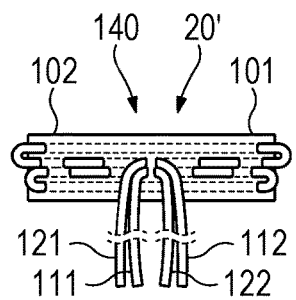
FIG. 54 shows a side view of another soft suture anchor in accordance with an embodiment.
Figure 55:
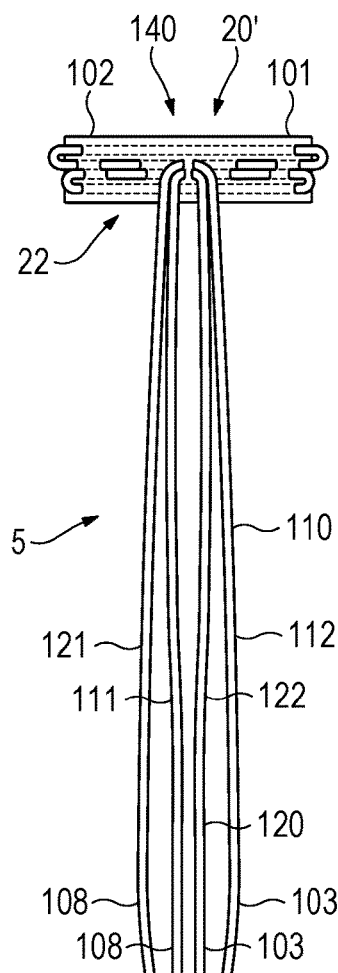
FIG. 55 shows a side view of the soft suture anchor in accordance with the embodiment of FIG. 54.

Referring to FIGS. 41-61, an embodiment of a method for making a soft suture anchor assembly 5 comprises:

providing a length of suture tape 100 comprising a warp and weft weave structure defining a tape first side 105 and a tape second side 106 opposite the tape first side 105 and a tape first end 101 and a tape second end 102 opposite the tape first end 101, as shown in FIG. 41, the suture tape 100 having a plurality of warp suture strands 103 woven as warp in the warp and weft configuration, each warp suture strand 103 including a warp suture first end 104 and a warp suture second end 109 opposite the warp suture first end 104, the suture tape 100 defining a central longitudinal axis X and a transverse axis Y perpendicular to the central longitudinal axis X, as shown in FIG. 41;

defining one of the warp suture strands 103 as a first deconstructed suture strand 110, the first deconstructed suture strand 110 comprising a first deconstructed suture strand first end 111 and a first deconstructed suture strand second end 112 opposite from the first deconstructed suture strand first end 111, defining a first deconstruction point 131 and a second deconstruction point 132 a predetermined distance from the first deconstruction point 131, the first deconstruction point 131 located adjacent the first deconstructed suture first end 111 of the first deconstructed suture strand 110 and the second deconstructed point 132 located adjacent the first deconstructed suture second end 112 of the first deconstructed suture strand 110, the first deconstructed suture strand 110 being spaced a predetermined distance from the central longitudinal axis X, as shown in FIG. 42-45;

defining another one of the warp suture strands 103 as a second deconstructed suture strand 120, the second deconstructed suture strand 120 comprising a second deconstructed suture strand first end 121 and a second deconstructed suture strand second end 122 opposite from the second deconstructed suture strand first end 121, defining a third deconstruction point 133 and a fourth deconstruction point 134 a predetermined distance from the third deconstruction point 133, the third deconstruction point 133 located adjacent the second deconstructed suture first end 121 of the second deconstructed suture strand 120 and the fourth deconstructed point 134 located adjacent the second deconstructed suture strand second end 122 of the second deconstructed suture strand 120, the second deconstructed suture strand 120 being spaced a predetermined distance from the central longitudinal axis X and opposite from the central longitudinal axis X from the first deconstructed suture strand 110, the first deconstruction point 131 and the third deconstruction point 133 being substantially aligned along a first transverse axis Y1 that is substantially perpendicular to the central longitudinal axis X, the second deconstruction point 132 and the fourth deconstruction point 134 being substantially aligned along a second transverse axis Y2 that is substantially perpendicular to the central longitudinal axis X, the suture tape 100 defining an anchor 20' between the first transverse axis Y1 and second transverse axis Y2, as shown in FIGS. 42-45;

withdrawing the first deconstructed suture strand first end 111 and the first deconstructed suture strand second end 112 of the first deconstructed suture strand 110 from the weft, as shown in FIGS. 44-45;

withdrawing the second deconstructed suture strand first end 121 and the second deconstructed suture strand second end 122 of the second deconstructed suture strand 120 from the weft, as shown in FIGS. 45-46;

trimming the tape first end 101 and tape second end 102 adjacent to the first transverse axis Y1 and second transverse axis Y2 and opposite from the anchor 20', as shown in FIGS. 46-47;

providing a lacing tool 40 comprising an elongated shaft 43 having a shaft first end 41 and a shaft second end 42, a handle 46 optionally formed in the shaft second end 42, the shaft first end 41 formed into a hook 45, the shaft first end 41 further comprising a lever 48 pivotally coupled to the shaft first end 41 adjacent the hook 45 operable to close the hook 45 in a first position and to open the hook 45 in a second position, as shown in FIG. 48;

engaging a first center location 141 of the anchor 20' substantially equidistant from the first transverse axis Y1 and second transverse axis Y2 with the hook 45 of the lacing tool 40 weaving one or more times through the anchor 20' as if a warp strand, terminating the weaving at about the first transverse axis Y1, as shown in FIG. 48;

placing the second deconstructed suture strand first end 121 into the hook 45 and closing the lever 48, as shown in FIG. 48;

pulling the hook 45 so as to pull the second deconstructed suture strand first end 121 through the weave of the anchor 20', removing the lacing tool 40 from the suture tape 100 such that the second deconstructed suture strand first end 121 extends out of the first center location 141, as shown in FIG. 49;

engaging a second center location 142 of the anchor 20' substantially equidistant from the first transverse axis Y1 and second transverse axis Y2 and adjacent to the first center location 141 with the hook 45 of the lacing tool 40 weaving one or more times through the anchor 20' as if a warp strand, terminating the weaving at about the first transverse axis Y1, as shown in FIG. 50;

placing the first deconstructed suture strand first end 111 into the hook 45 and closing the lever 48, as shown in FIG. 50;

pulling the hook 45 so as to pull the first deconstructed suture strand first end 111 through the weave of the anchor 20', removing the lacing tool 40 from the suture tape 100 such that the first deconstructed suture strand first end 111 extends out of the second center location 142, as shown in FIG. 51;

engaging a third center location 143 of the anchor 20' substantially equidistant from the first transverse axis Y1 and second transverse axis Y2 with the hook 45 of the lacing tool 40 weaving one or more times through the anchor 20' as if a warp strand, terminating the weaving at about the second transverse axis Y2, as shown in FIG. 52 placing the second deconstructed suture strand second end 122 into the hook 45 and closing the lever 48, as shown in FIG. 52;

pulling the hook 45 so as to pull the second deconstructed suture strand second end 122 through the weave of the anchor 20', removing the lacing tool 40 from the suture tape 100 such that the second deconstructed suture strand second end 122 extends out of the third center location 143, as shown in FIG. 53;

engaging a fourth center location 144 of the anchor 20' substantially equidistant from the first transverse axis Y1 and second transverse axis Y2 and adjacent to the third center location 143 with the hook 45 of the lacing tool 40 weaving one or more times through the anchor 20' as if a warp strand, terminating the weaving at about the second transverse axis Y2, as shown in FIG. 53; and placing the first deconstructed suture strand second end 112 into the hook 45 and closing the lever 48, as shown in FIG. 53;

pulling the hook 45 so as to pull the first deconstructed suture strand second end 112 through the weave of the anchor 20', removing the lacing tool 40 from the suture tape 100 such that the first deconstructed suture strand second end 112 extends out of the fourth center location 144 permitting a deployed anchor 22, as shown in FIG. 56.

An embodiment of a method for using a soft suture anchor assembly 5 comprises:

placing the deployed anchor 22 into a pilot hole 72 drilled into a bone 70, the pilot hole 72 defining a base 73, as shown in FIG. 57;

engaging an insertion and retention tool 74 to hold the anchor 20' at about the base 73; and putting tension on the first deconstructed suture strand first end 111, first deconstructed suture strand second end 112, second deconstructed suture strand first end 121, and second deconstructed suture strand second end 122 operable to cinch and/or bunch the anchor 20' such that the deployed anchor 22 engages the pilot hole 72, as shown in FIGS. 57-58.

The tool 74 may be any suitable instrument that is operable to push and/or hold the anchor 20 in the pilot hole 72. The tool 74 may comprise an elongated member with an end that may be received into the pilot hole 72.

It is appreciated that wherein the deployed anchor 22 may be engaged predominantly by bunching, as defined below, the tool 74 may be used to push the anchor 24 to about the base 73 and then removed prior to putting tension on the first deconstructed suture strand first end 111, first deconstructed suture strand second end 112, second deconstructed suture strand first end 121, and second deconstructed suture strand second end 122 operable to cinch and/or bunch the anchor 20' such that the deployed anchor 22 engages the pilot hole 72;

It is appreciated that the first center location 141, second center location 142, third center location 143, and fourth center location 144 may be co-located at one center location 140 such that the first and second deconstructed suture strand ends 111, 112, 121, 122 extend from the same center location 140 of the anchor 20'. Skilled persons will readily recognize, further in view of FIG. 57, that center location 140 is also a "hold region," that is, a region that is optimally held in place as ends 121 and 122 are pulled to set anchor 20 into surrounding bone.

An embodiment of a method for using a soft suture anchor assembly 5 further comprising:

removing one of the first deconstructed suture strand 110 and second deconstructed suture strand 120 from the deployed anchor 22 by putting tension on one of the first and second ends 111,112,121, 122 allowing one of the first deconstructed suture strand 110 and second deconstructed suture strand 120 to slide out of the anchor 20', as shown in FIGS. 59-61.

It is appreciated that the size of the deployed anchor 22 may be dependent, in-part, on the suture tape width and the length of the anchor 20'. A longer anchor 20' will create a larger anchor profile as compared with a smaller anchor 20' wherein the distance between the first penetration point 131 and second penetration point 132 defines the length of the anchor 20'.

It is appreciated that one or more warp suture strands 103 may be deconstructed from the suture tape 100 as described above so as to provide a desired number of deconstructed suture strand ends for securing tissue and the like. In the above embodiment of the soft suture anchor, two deconstructed strands is shown by way of example. It is understood and appreciated that an embodiment of the soft suture anchor may comprise one deconstructed suture strand, wherein other embodiments of the soft suture anchor may comprise a plurality of deconstructed suture strands.

Cinching is defined herein as a squeezing together of the anchor 20' substantially due to a slippage or movement of a deconstructed suture strand with respect to other suture strands such that the anchor 20' is drawn together. For example, referring to the embodiment above, tension on the first deconstructed suture strand first end 111 and on the first deconstructed suture strand second end 112 may cause the first deconstructed suture strand 103 to slip relative to the other suture strands in the anchor 20' operable to squeeze together the anchor 20' towards the center location 140 without the requirement of cooperative engagement with another structure, such as, whether or not the deployed anchor 22 is in a pilot hole 72.

Bunching is defined as a squeezing together of the anchor 20' substantially due to other than a slippage or movement of a deconstructed suture strand with respect to other suture strands. By way of example, bunching may be caused by the operative frictional engagement of the anchor 20' with another structure, such as with the bore of the pilot hole 72. For example, referring to the embodiments above, tension on the first deconstructed suture strand first end 111 and on the first deconstructed suture strand second end 112 may cause the anchor 20' to drag against the bore of the pilot hole 72 so as to cause the anchor 20' to squeeze together and wedge against the bore of the pilot hole 72 sufficient to prevent pullout of the deployed anchor 22 from the pilot hole 72.

It is understood that in certain embodiments, the predominate mechanism for anchoring the deployed anchor 22 into the pilot hole 72 is cinching, bunching, or a combination of cinching and bunching. It is understood that the depth of the pilot hole 72 may be less where cinching is the predominant squeezing mechanism on the anchor 20' as compared to bunching where dragging along the bore of the pilot hole 72 may be required to affect the squeezing of the deployed anchor 22.

In accordance with embodiments, the first deconstructed suture strand 110 and second deconstructed suture strand 120 may move relative to the anchor 20' when tension on one or more of the first and second ends 111,112,121, 122 is applied such that the predominate mechanism for anchoring the deployed anchor 22 into the pilot hole 72 is cinching.

In accordance with other embodiments, the first deconstructed suture strand 110 and second deconstructed suture strand 120 may not move relative to the anchor 20' when tension on one or more of the first and second ends 111, 112,121, 122 is applied such that the predominate mechanism for anchoring the deployed anchor 22 into the pilot hole 72 is bunching.

In accordance with yet other embodiments, the first deconstructed suture strand 110 and second deconstructed suture strand 120 may move and may not move relative to the anchor 20' when tension on one or more of the first and second ends 111,112,121, 122 is applied such that the predominate mechanism for anchoring the deployed anchor 22 into the pilot hole 72 is a combination of cinching and bunching.

Wavy Tape Suture Anchor

FIGS. 68-71 are side views of an embodiment of a soft suture anchor 6 including an anchor 24 with suture ends 211, 212 extending therefrom.

Referring to FIGS. 62-71, a soft suture anchor 6 comprises a length of wavy suture tape 200 having a suture tape first end 201 and a suture tape second end 202 opposite the suture tape first end 201, as shown in FIG. 62. The wavy suture tape 200 comprises a plurality of warp suture strands 203 woven in a warp configuration (where the strands are generally parallel to but having a generally sinusoidal path relative to the longitudinal central axis X) and weft suture strands (not shown, where the strands are substantially perpendicular to the longitudinal axis X) woven in a weft configuration.

The ends of one or more warp suture strands 203 are deconstructed from the weave of the suture tape 200, and hereinafter referred to as a deconstructed suture strand 208, leaving an anchor 20' of the warp suture strands 203 remaining in the weave, as shown in FIGS. 63-67, defining in part the anchor 24, as shown in FIGS. 68-71. The deconstructed suture strand 208 comprise a deconstructed suture strand first end 211 and a deconstructed suture strand second end 212 opposite from the deconstructed suture strand first end 211. Tension on the deconstructed suture strand first end 211 and the deconstructed suture strand second end 212 of the one or more deconstructed suture strands 208 causes the anchor 20' to cinch and/or bunch together to present a profile such that the anchor 20' may engage a pilot hole 72 in bone 70 which is resistant to pull-out.

In accordance with embodiments, the wavy suture tape 200 is made by applying differential tension across elements of a weaving machine. The structure of the wavy suture tape may be produced, among other ways, by varying the tension between adjacent warp or weft threads. This tension variation may induce a generally sinusoidal or undulating pattern in the warp. The frequency and amplitude of the undulating pattern may be controlled by adjusting parameters on the weaving machine.

The wavy tape 200 may present a larger or more three-dimensional profile as compared to a straight suture tape, such as suture tape 100 presented above, and as such, may better engage and better resist pullout from a pilot hole 72.

In accordance with embodiments, the wavy suture tape is made entirely of biocompatible suture material, such as, but not limited to UHMWPE (ultra-high molecular weight polyethylene), polyester, mixtures thereof, and bio absorbable compounds and mixtures such as, but not limited to polybutylene succinate, polycaprolatone (PCL), polyglycolic acid (PGA), and polylactic acid (PLA). In accordance with an embodiment, one or more of the warp strands may be UHMWPE with the remainder being polyester, by way of example. In accordance with an embodiment, one or more individual suture strands may be woven in the warp orientation and used as the suture strands that extend from the anchor, in a secondary process after the production of a suture tape. In accordance with an embodiment, one or more individual UHMWPE strands may be weaved in the warp orientation and used as the suture strands that extend from the anchor, in a secondary process after the production of a suture tape.

Referring to FIGS. 62-71, there is shown a length of wavy suture tape 200 having a suture tape first end 201 and a suture tape second end 202 opposite the suture tape first end 201, as shown in FIG. 62. The wavy suture tape 200 comprises a plurality of suture strands 203 woven in a warp configuration, where the strands are generally parallel to but having a generally sinusoidal path relative to the longitudinal central axis X.

Figure 69:
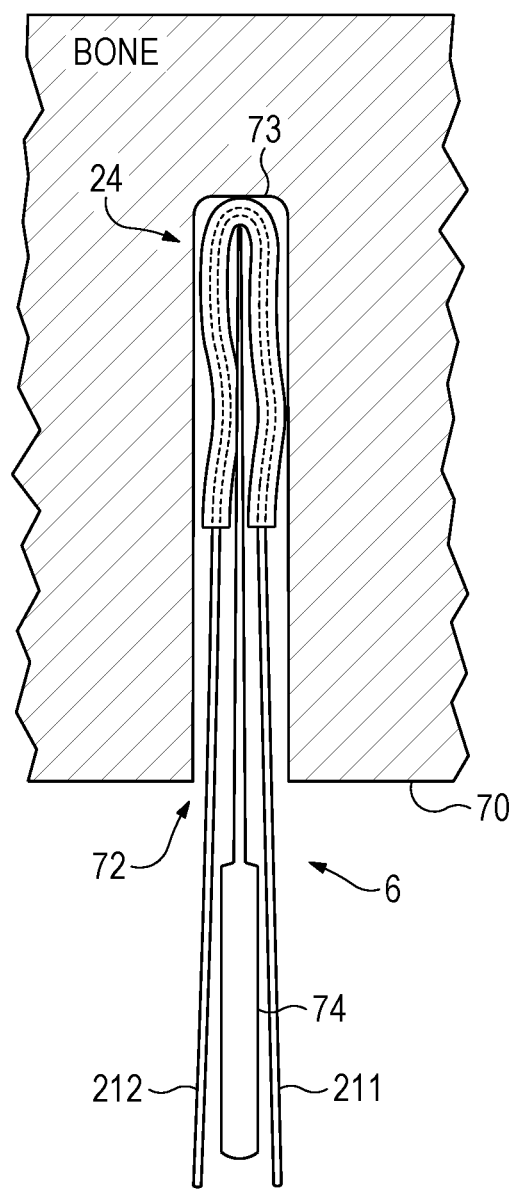
FIG. 69 shows a side view of a soft suture anchor in accordance with an embodiment.

In this embodiment, the ends of one or more warp suture strands 203 are deconstructed from the weave of the suture tape 200, and hereinafter referred to as deconstructed suture strands 208, defining an anchor 20' comprising a portion of the warp suture strands remaining in the weave, as shown in FIGS. 63-67. The deconstructed suture strands 208 comprise a deconstructed suture strand first end 211 and a deconstructed suture strand second end 212 opposite from the deconstructed suture strand first end 211. The anchor 20', defining in-part an anchor 24, may be disposed in a pilot hole 72, such as a pilot hole 72 resulting from drilling into bone 70, as shown in FIG. 69. Tension on the deconstructed suture strand first end 211 and the deconstructed suture strand second end 212 causes the anchor 20' to cinch and/or bunch and present a profile so as to wedge the anchor 24 into the pilot hole 72 which is resistant to pull-out, as shown in FIG. 70-71. With the anchor 24 anchored into the bone 70, the deconstructed suture strand first end 211 and the deconstructed suture strand second end 212 may be used, for example, to engage tissue and hold it against the bone 70 for healing, such as, but not limited to, tendon reattachment.

Figure 65:
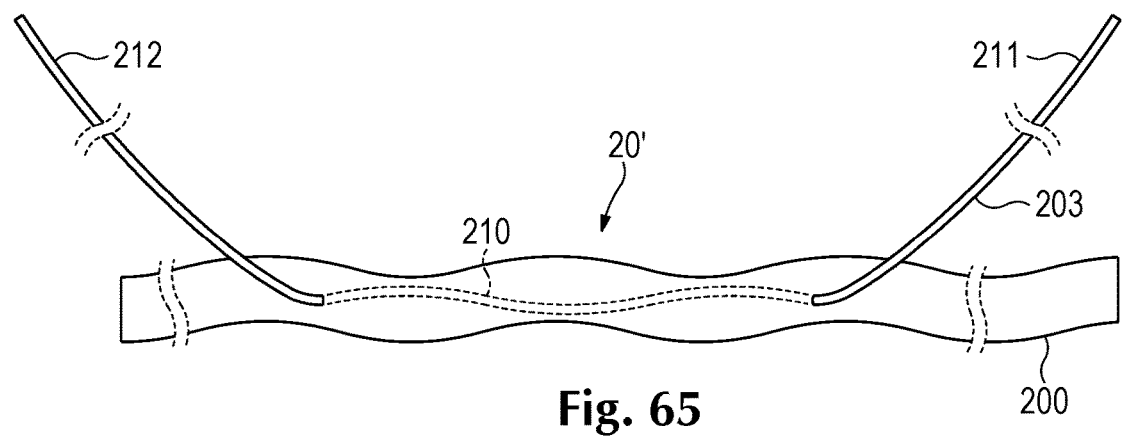
FIG. 65 shows a side view of a wavy suture tape construct in accordance with an embodiment.
Figure 66:
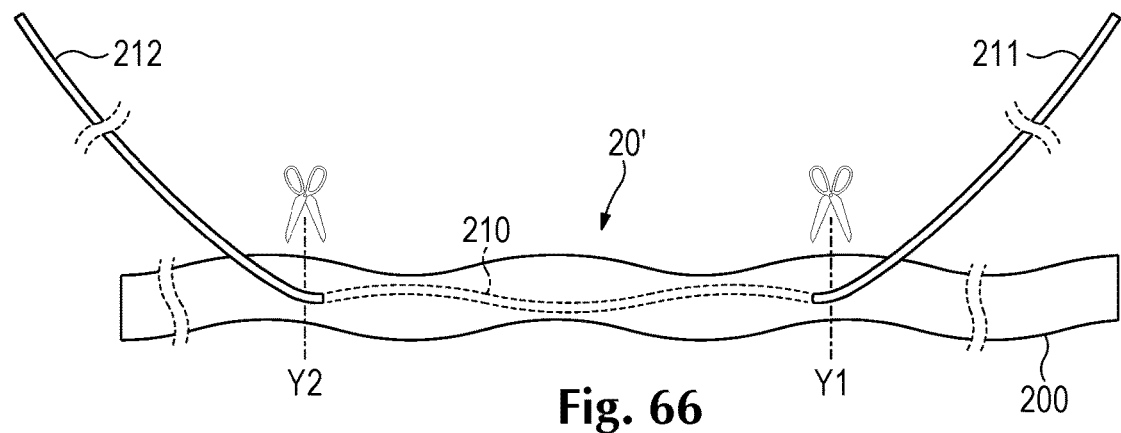
FIG. 66 shows a side view of a wavy suture tape construct in accordance with an embodiment.
Figure 67:
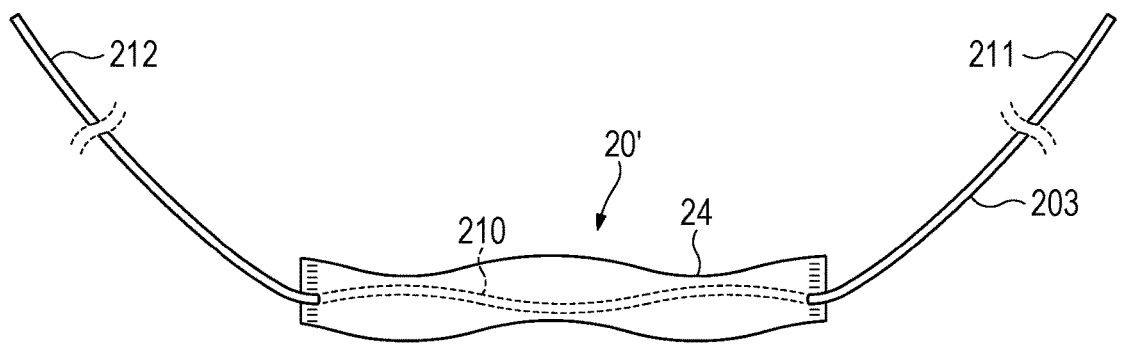
FIG. 67 shows a side view of a soft suture anchor in accordance with an embodiment.
Figure 68:
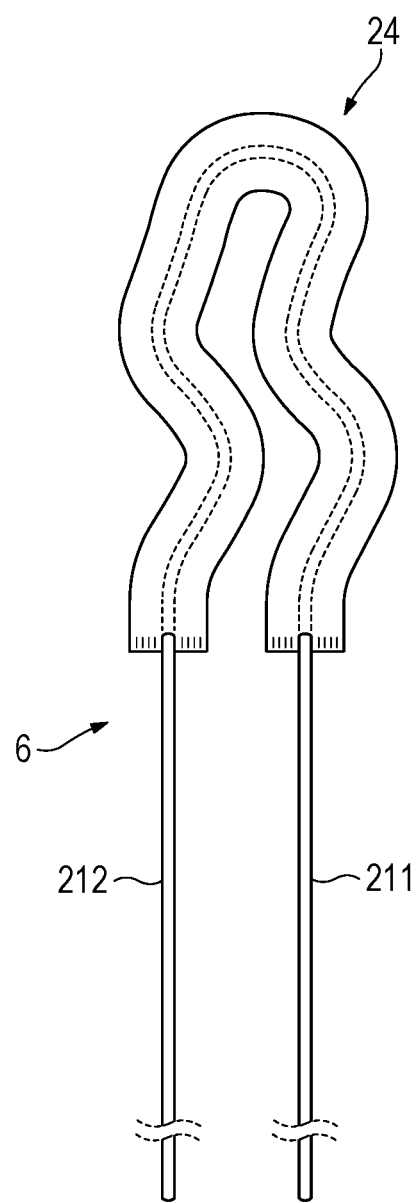
FIG. 68 shows a side view of a soft suture anchor in accordance with an embodiment.

Referring to FIGS. 62-71, an embodiment of a method for making a soft suture tape anchor 6 comprises:

providing a length of wavy suture tape 200 comprising a warp and weft weave structure defining a tape first side 105 and a tape second side 106 opposite the tape first side 105 and a tape first end 201 and a tape second end 202 opposite the tape first end 201, as shown in FIG. 62, the wavy suture tape 200 having a plurality of warp suture strands 203 woven as warp in the warp and weft configuration, each warp suture strand 203 including a warp suture first end 204 and a warp suture second end 209 opposite the warp suture first end 204, the wavy suture tape 200 defining a central longitudinal axis X and a transverse axis Y perpendicular to the central longitudinal axis X, as shown in FIG. 62;

defining one of the warp suture strands 203 as a deconstructed suture strand 208, the deconstructed suture strand 208 comprising a deconstructed suture strand first end 211 and a deconstructed suture strand second end 212 opposite from the deconstructed suture strand first end 211, defining a first deconstruction point 131 and a second deconstruction point 132 a predetermined distance from the first deconstruction point 131, the first deconstruction point 131 located adjacent the deconstructed suture first end 211 of the deconstructed suture strand 208 and the second deconstructed point 132 located adjacent the deconstructed suture second end 212 of the deconstructed suture strand 208, as shown in FIG. 63-65;

withdrawing the deconstructed suture strand first end 211 and the deconstructed suture strand second end 212 of the deconstructed suture strand 208 from the weft, of the wavy suture tape 200, as shown in FIGS. 63-64;

trimming the tape first end 201 and tape second end 202 adjacent to a first transverse axis Y1 and a second transverse axis Y2 and opposite from the anchor 20', as shown in FIG. 66, defining an anchor 24, as shown in FIG. 67.

An embodiment of a method for using a soft suture tape anchor 6 comprises:

placing the anchor 24 into a pilot hole 72 drilled into a bone 70, the pilot hole 72 defining a base 73, as shown in FIG. 69;

engaging a tool 74 to push the anchor 24 to about the base 73; and putting tension on the warp suture first end 211 and warp suture second end 212 operable to cinch and/or bunch the anchor 20' such that the anchor 24 engages the pilot hole 72, as shown in FIGS. 69-71.

The tool 74 is any suitable instrument that is operable to push the anchor 24 in the pilot hole 72. The tool 74 may comprise an elongated member with an end that may be received into the pilot hole 72.

It is appreciated that the size of the anchor 24 may be dependent, in-part, on the suture tape width and the length of the anchor 20'. A longer anchor 20' will create a larger anchor profile as compared with a smaller anchor 20' wherein the distance between the first penetration point 131 and second penetration point 132 defines the length of the anchor 20'.

It is appreciated that more than one warp suture strand 203 may be deconstructed from the wavy suture tape 200 as described above so as to provide additional suture ends for securing tissue and the like.

The above embodiment is described as the suture tape comprising a weave construction. It is understood and appreciated that other constructions are suitable for the particular purpose. By way of example, the suture tape may comprise a flat braid of suture strands. Regarding a braid, one or more of the suture strands that are braided together is identified as a deconstructed suture strand with the embodiments comprising a braid being practiced substantially the same as for the embodiments comprising a weave.

Skilled persons will readily recognized that the bunching portion variants 34 and 20' may each be termed an "anchor" that has an undeployed state, in the form of a ribbon or sheet of flexible material, as shown in FIGS. 56 and 57, and that may be compacted into a deployed state, above termed "deployed anchor 22" as shown in FIG. 58, by pulling on deconstructed strands 108, 110, 111, 121 and 122 which may be termed "deployment strands." It may further be noted that the deployment strands 108 are engaged to the first end 101 and second end 102 of bunching portion (which may also be termed, "the anchor in its undeployed state") 34 by being looped around the ends 101, 102 (which form the periphery of the anchor or anchor 34; more specifically end 101 is a first peripheral location and end 102 is a second peripheral location, opposed to the first peripheral location), with both ends of each deployment strand 108, 110, 111, 121 and 122 threaded through and exiting the anchor or anchor 20' at a central location 140.

Figure 72:
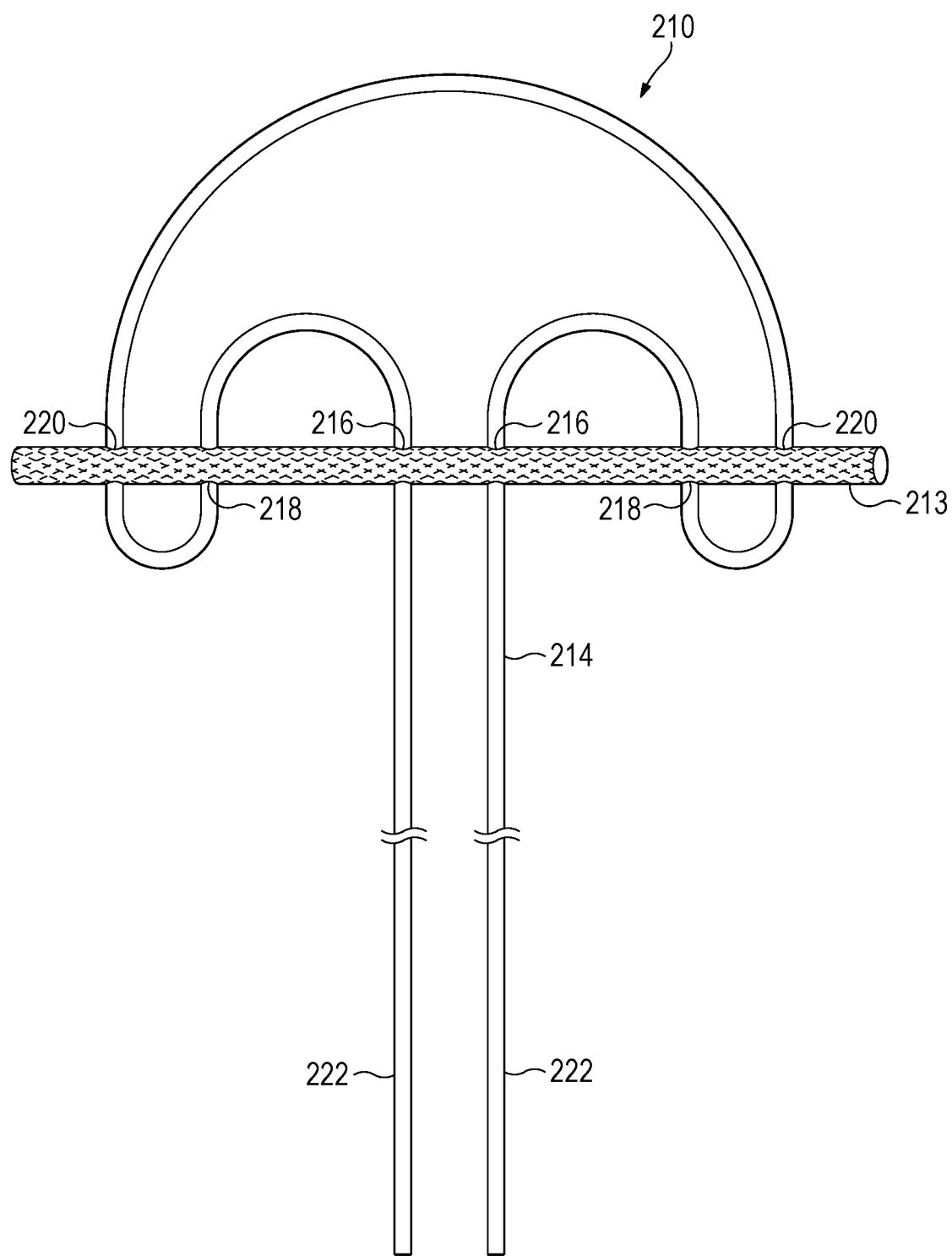
FIG. 72 shows a side view of a soft anchor according to still another preferred embodiment.

Referring to FIG. 72, in an additional preferred embodiment and method, a construct 210 is provided having a cross-member suture 213 and a cinching suture 214. Cinching suture 214 is engaged to cross-member suture 213 at two central points 216, two lateral mid-points 218 and two lateral points 220. Two cinching suture ends 222 extend outwardly from the two central points 216. In an alternative preferred embodiment, needles are attached to suture ends 222.

Figures 73, 74:
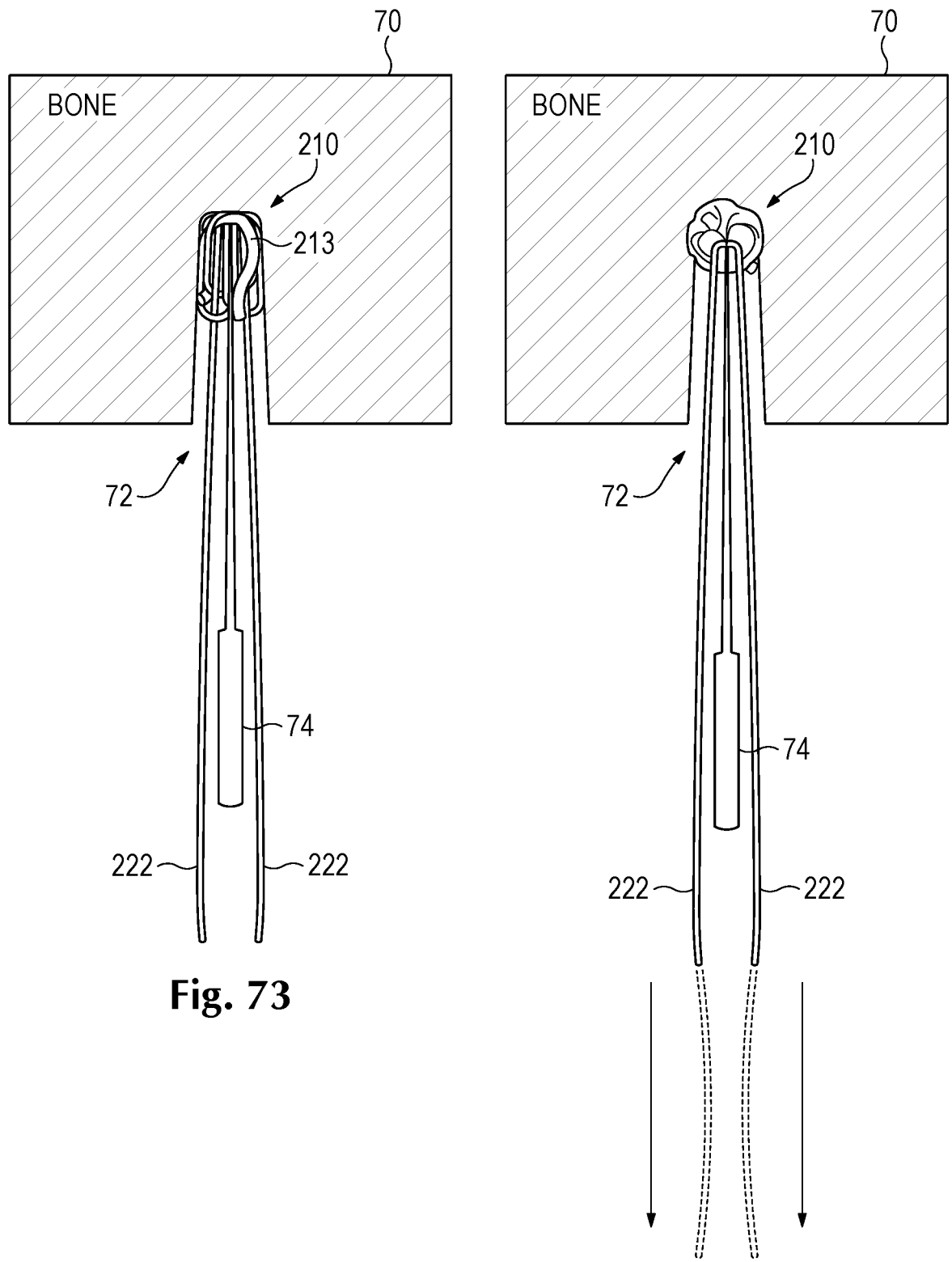
FIG. 73 shows a side view of the soft anchor of FIG. 72 inserted into a pilot hole in bone, prior to being cinched into a ball.
FIG. 74 shows a side view of the soft anchor of FIG. 72 inserted into a pilot hole in bone, after being cinched into a ball.

Referring to FIGS. 73 and 74, to introduce construct 210 into a pilot hole 72, the tip of an insertion tool 74 is placed at cross-member suture 213 between central points 216 and is used to push construct 210 into the pilot hole 72 with more lateral portion of cross-member suture 213 extending from the insertion tool tip back toward the hole opening. When the tip of insertion tool 74 is at a target location, the suture ends 222 are pulled, causing engagement points 218 and 220 to be pulled toward the tip of tool 74, causing construct 210 to cinch or ball up, as shown in FIG. 74. In an alternative preferred embodiment, additional suture strands, similar in construction to cinching suture 74, may be included, and engaged with cross member suture 213, so that after the anchor is set, a greater number than two strands emerge from the pilot hole 72. In one embodiment a single additional suture, results in two additional strands (that is suture ends) emerging from pilot hole 72, for four strands in all. In a further embodiment two additional sutures result in six strands emerging from hole 72.

One advantage of construct 210 is that cross-member suture 213 and cinching suture 214 can be made of differing materials. In one preferred embodiment cross-member suture 213 is a #5 polyester suture, whereas suture 214 is a #0 UHMWPE suture.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

The invention claimed is:

1. A method of anchoring suture to bone, with an anchor set at a target location, comprising:
   a. creating a pilot hole in said bone;
   b. providing an insertion tool sized to enter said pilot hole and having a tip;
   c. providing a soft anchor construct, including:
      i. a cross-member suture, comprising braided suture material;
      ii. a cinching suture, having a first end and a second end;
      iii. wherein said cinching suture extends from said first end to said cross-member suture, and traverses through said cross-member suture at a first central point;
      iv. wherein said cinching suture extends from said first central point to a first intermediate point, that is displaced in a first direction from said first central point, and traverses said cross-member suture at said first intermediate point;
      v. wherein said cinching suture further extends from said first intermediate point to a first lateral point, that is displaced from said first intermediate point in said first direction and traverses through said cross-member suture at said first lateral point;
      vi. wherein said cinching suture further extends from said first lateral point to a second lateral point, opposed to said first lateral point, and traverses through said cross-member suture at said second lateral point;

vii. wherein said cinching suture further extends from said second lateral point to a second intermediate point, that is displaced in said first direction from said second lateral point and traverses through said cross-member suture at said second intermediate point;

viii. wherein said cinching suture further extends from said second intermediate point to a second central point, that is displaced in said first direction from said second intermediate point, and traverses said cross-member suture at said second intermediate point; and ix. wherein said cinching suture further extends from said second central point to said second end, said cinching suture not traversing said cross-member suture in any further locations, other than as stated above, and traversing each said location a single time only;

d. using said insertion tool tip to engage said cross-member suture between said first and second central points and to push said suture construct to said target location in said pilot hole;

e. while holding said suture construct in place with said insertion tool, pulling on said ends of said cinching suture until said cross-member suture and portions of said cinching suture that are engaged to said cross-member suture cinch up into a ball, thereby setting into said pilot hole at said target location.

2. The method of claim 1, wherein said target location is at the bottom of said pilot hole.

3. The method of claim 1, wherein said cross-member suture has a greater diameter than said cinching suture.

4. The method of claim 1, wherein said cross-member suture is a #5 suture.

5. The method of claim 1, wherein said cinching suture is a #2 suture.

6. The method of claim 1, wherein said cross-member suture has a diameter at least 1.2 times that of the diameter of said cinching suture.

7. The method of claim 1, wherein said cross-member suture comprises polyester.

8. The method of claim 1, wherein said cinching suture comprises ultra-high molecular weight polyethylene.

9. The method of claim 1, wherein said cross-member suture is a round braided suture.

* * * * *